United States Patent
Tsugo

(10) Patent No.: US 10,714,214 B2
(45) Date of Patent: Jul. 14, 2020

(54) MEDICAL ASSISTANCE DEVICE, OPERATION METHOD AND OPERATION PROGRAM FOR MEDICAL ASSISTANCE DEVICE, AND MEDICAL ASSISTANCE SYSTEM

(71) Applicant: FUJIFILM Corporation, Tokyo (JP)

(72) Inventor: Akinari Tsugo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1351 days.

(21) Appl. No.: 14/843,952

(22) Filed: Sep. 2, 2015

(65) Prior Publication Data
US 2016/0085929 A1  Mar. 24, 2016

(30) Foreign Application Priority Data
Sep. 24, 2014  (JP) ................................ 2014-193297

(51) Int. Cl.
*G16H 15/00* (2018.01)
*G16H 50/20* (2018.01)

(52) U.S. Cl.
CPC ............. *G16H 15/00* (2018.01); *G16H 50/20* (2018.01); *Y02A 90/26* (2018.01)

(58) Field of Classification Search
CPC ......... G16H 15/00; G16H 50/20; Y02A 90/26
See application file for complete search history.

(56) References Cited

U.S. PATENT DOCUMENTS 5,347,453 A * 9/1994 Maestre ............... A61J 7/0481
705/2
8,417,548 B2  4/2013 Araki et al.
(Continued)

FOREIGN PATENT DOCUMENTS

JP  2003126045  5/2003
JP  2009032091  2/2009
(Continued)

OTHER PUBLICATIONS

"Office Action of Japan Counterpart Application," with machine English translation thereof, dated Feb. 14, 2018, p. 1-p. 8, in which the listed references were cited.
(Continued)

*Primary Examiner* — Linh Giang Le
(74) *Attorney, Agent, or Firm* — JCIPRNET

(57) ABSTRACT

There are provided a medical assistance device, an operation method of a medical assistance device, a non-transitory computer-readable recording medium, and a medical assistance system capable of improving work efficiency by reducing the burden on a user. A recommended data range output unit receives a program ID of a diagnostic assistance program from a request receiving unit. The recommended data range output unit reads a recommended data range corresponding to the received program ID from a recommended data range list, and transmits the recommended data range to a screen generation unit. The screen generation unit includes a check box and a period designating bar for designating designated data items and a designated data period, which form a designated data range, and generates a medical data display screen on which displays of recommended data items and a recommended data period, which forms a recommended data range, are made.

13 Claims, 24 Drawing Sheets

(56) References Cited

U.S. PATENT DOCUMENTS

| | | |
|---|---|---|
| 9,858,392 B2 | 1/2018 | Janevski et al. |
| 2004/0059215 A1 | 3/2004 | Nishimura et al. |
| 2012/0089893 A1* | 4/2012 | Bousamra .......... A61B 5/14532 |
| | | 714/807 |
| 2012/0290324 A1 | 11/2012 | Ribbing et al. |
| 2018/0089392 A1 | 3/2018 | Janevski et al. |

FOREIGN PATENT DOCUMENTS

| | | |
|---|---|---|
| JP | 2009247688 | 10/2009 |
| JP | 2009273558 | 11/2009 |
| JP | 2010142273 | 7/2010 |
| JP | 2011039624 | 2/2011 |
| JP | 2011520206 | 7/2011 |
| JP | 2013513845 | 4/2013 |
| WO | 2011048812 | 4/2011 |

OTHER PUBLICATIONS

"Office Action of Japan Counterpart Application," with machine English translation thereof, dated Jul. 26, 2017, p. 1-p. 9, in which the listed references were cited.

\* cited by examiner

FIG. 8

| DISEASE (DISEASE ID) | DISPLAY ITEMS | | DIAGNOSTIC ASSISTANCE PROGRAM (PROGRAM ID) |
|---|---|---|---|
| DISEASE A (D1) | DOSING | DRUG A<br>DRUG B | DIAGNOSTIC ASSISTANCE PROGRAM (PR1)<br>DIAGNOSTIC ASSISTANCE PROGRAM (PR2)<br>DIAGNOSTIC ASSISTANCE PROGRAM (PR3)<br>DIAGNOSTIC ASSISTANCE PROGRAM (PR4)<br>⋮ |
| | VITAL SIGNS | BLOOD PRESSURE (TOP)<br>BLOOD PRESSURE (BOTTOM) | |
| | TEST SUBSTANCE EXAMINATIONS | BIOCHEMICAL TEST A<br>BIOCHEMICAL TEST B | |
| | IMAGE EXAMINATIONS | CT EXAMINATION | |
| DISEASE B (D2) | DOSING | DRUG A<br>DRUG C | DIAGNOSTIC ASSISTANCE PROGRAM (PR20)<br>DIAGNOSTIC ASSISTANCE PROGRAM (PR21)<br>⋮ |
| | VITAL SIGNS | BLOOD PRESSURE (TOP)<br>BLOOD PRESSURE (BOTTOM) | |
| | TEST SUBSTANCE EXAMINATIONS | BLOOD TEST E<br>BIOCHEMICAL TEST F | |
| | IMAGE EXAMINATIONS | ULTRASONIC EXAMINATION | |
| COMPLEX DISEASE AB (D1 + D2) | DOSING | DRUG A<br>DRUG B<br>DRUG C | DIAGNOSTIC ASSISTANCE PROGRAM (PR100)<br>⋮ |
| | VITAL SIGNS | BLOOD PRESSURE (TOP)<br>BLOOD PRESSURE (BOTTOM) | |
| | TEST SUBSTANCE EXAMINATIONS | BIOCHEMICAL TEST A<br>BIOCHEMICAL TEST B<br>BLOOD TEST E<br>BIOCHEMICAL TEST F<br>BIOCHEMICAL TEST G | |
| | IMAGE EXAMINATIONS | CT EXAMINATION<br>ULTRASONIC EXAMINATION | |

FIG. 12

| DIAGNOSTIC ASSISTANCE PROGRAM (PROGRAM ID) | RECOMMENDED DATA RANGE | | |
|---|---|---|---|
| | RECOMMENDED DATA ITEM | | RECOMMENDED DATA PERIOD |
| DIAGNOSTIC ASSISTANCE PROGRAM (PR1) | DOSING | DRUG A | ONE MONTH FROM DOSING DATE OF DRUG A |
| | VITAL SIGNS | BLOOD PRESSURE (TOP)  PULSE<br>BLOOD PRESSURE (BOTTOM)  BODY TEMPERATURE | |
| | TEST SUBSTANCE EXAMINATIONS | BIOCHEMICAL TEST A | |
| | IMAGE EXAMINATIONS | NONE | |
| DIAGNOSTIC ASSISTANCE PROGRAM (PR2) | DOSING | DRUG C | TEN DAYS FROM SURGERY DATE OF X SURGERY |
| | VITAL SIGNS | BLOOD PRESSURE (TOP)  PULSE<br>BLOOD PRESSURE (BOTTOM) | |
| | TEST SUBSTANCE EXAMINATIONS | BLOOD TEST E | |
| | IMAGE EXAMINATIONS | ULTRASONIC EXAMINATION | |

| DIAGNOSTIC ASSISTANCE PROGRAM (PROGRAM ID) | RECOMMENDED DATA RANGE ~125 | | | | |
|---|---|---|---|---|---|
| | RECOMMENDED DATA ITEM | | | RECOMMENDED DATA PERIOD | |
| | ESSENTIAL DATA ITEM | | ALLOWABLE DATA ITEM | ESSENTIAL DATA PERIOD | ALLOWABLE DATA PERIOD |
| DIAGNOSTIC ASSISTANCE PROGRAM (PR1) | DOSING | DRUG A | DRUG B | TWO WEEKS FROM DOSING DATE OF DRUG A | THREE TO FOUR WEEKS FROM DOSING DATE OF DRUG A |
| | VITAL SIGNS | BLOOD PRESSURE (TOP) PULSE BLOOD PRESSURE (BOTTOM) BODY TEMPERATURE | VITAL SIGNS HEART RATE | | |
| | TEST SUBSTANCE EXAMINATIONS | BIOCHEMICAL TEST A | BIOCHEMICAL TEST B BIOCHEMICAL TEST C | | |
| | IMAGE EXAMINATIONS | NONE | NONE | | |

FIG. 21

| ITEM | | DEFAULT DATA |
|---|---|---|
| DOSING | DRUG A | 100 mg ONE MONTH |
| | DRUG B | 50 mg ONE MONTH |
| | ⋮ | ⋮ |
| VITAL SIGNS | BLOOD PRESSURE (TOP) | 125 mmHg |
| | BLOOD PRESSURE (BOTTOM) | 80 mmHg |
| | BODY TEMPERATURE | 36.5°C |
| | PULSE | 70 TIMES/MINUTE |
| | ⋮ | ⋮ |
| TEST SUBSTANCE EXAMINATIONS | BIOCHEMICAL TEST A | 20 IU/l |
| | BIOCHEMICAL TEST B | 15 IU/l |
| | ⋮ | ⋮ |

137

MEDICAL ASSISTANCE DEVICE, OPERATION METHOD AND OPERATION PROGRAM FOR MEDICAL ASSISTANCE DEVICE, AND MEDICAL ASSISTANCE SYSTEM

CROSS-REFERENCE TO RELATED APPLICATIONS

The present application claims priority under 35 U.S.C. §119 to Japanese Patent Application No. 2014-193297, filed on Sep. 24, 2014. Each of the above application(s) is hereby expressly incorporated by reference, in its entirety, into the present application.

BACKGROUND OF THE INVENTION

1. Field of the Invention

The present invention relates to a medical assistance device, an operation method of a medical assistance device, a non-transitory computer-readable recording medium, and a medical assistance system.

2. Description of the Related Art

In the medical field, a medical assistance device that generates a medical data display screen to display medical data, such as examination data or measurement data acquired in the course of treatment for a patient, is known. Among these medical assistance devices, there is a medical assistance device having a function of using a diagnostic assistance program in addition to a function of generating the medical data display screen. The diagnostic assistance program is executed to perform calculation using medical data as input data and output the calculation result as diagnostic assistance information to assist the diagnosis of a patient. It is expected that the diagnostic assistance program will be variously developed by the development companies according to the type of disease or the like in the future.

JP2009-273558A discloses a medical checkup assistance device using a medical checkup assistance program that performs calculation using the medical data of a plurality of items recorded in time series, such as a cholesterol level, a blood sugar level, blood pressure, the amount of smoking, and sleeping hours, as input data and outputs the risk of developing a disease as medical checkup assistance information. In the technique disclosed in JP2009-273558A, a user designates a period, which is to be used for input data, of the medical data in the entire course of treatment for the patient. Then, using the medical checkup assistance program, the risk of developing the disease is calculated based on the medical data of the period designated by the user.

SUMMARY OF THE INVENTION

Incidentally, each diagnostic assistance program is created for each purpose of diagnostic assistance, such as the analysis of a specific disease. Therefore, a recommended data range that is recommended for the range of medical data to be used for input data should be set in advance.

On the other hand, since the content of diagnostic assistance information may change depending on the range to be used for input data, a user himself or herself may want to designate a range to be used for input data. Specifically, this is a case in which the user wants to designate the items of specific medical data in which the user is interested or a case in which the user wants to designate a period of medical data to be used for the execution of a diagnostic assistance program as disclosed in JP2009-273558A.

In such an environment of use of a diagnostic assistance program, the user should remember a recommended data range so that a range designated by the user (hereinafter, referred to as a designated data range) matches a recommended data range and pay attention so as not to designate a range that is different from the recommended data range.

However, the advances of medical research and the innovation of medical technology in recent years, such as the development of new drugs and establishment of new knowledge, has been remarkable. Moreover, with the development of information technology, also in the medical field, a large amount of various kinds of information has been collected. In other words, the accumulation of so-called big data is in progress. In order to adapt to such a trend, it is expected that many kinds of diagnostic assistance programs will be developed day by day and will become obsolete quickly. In such a situation in which there are many types of diagnostic assistance programs and the obsolescence is quick, it is unreasonable for the user to remember the recommended data range for each type of diagnostic assistance program.

Thus, since the designation of a range gives a large burden to the user, work efficiency has been reduced.

It is an object of the invention to provide a medical assistance device capable of improving work efficiency by reducing the burden on a user, an operation method of a medical assistance device, a non-transitory computer-readable recording medium, and a medical assistance system.

In order to solve the above-mentioned problem, according to an aspect of the invention there is provided a medical assistance device, including: a program selection receiving unit that receives a selection of a diagnostic assistance program to be used among a plurality of diagnostic assistance programs that are executed to perform calculation using medical data of a patient as input data and output a result of the calculation as diagnostic assistance information for assisting diagnosis of the patient; a recommended data range output unit that acquires a recommended data range corresponding to the diagnostic assistance program received by the program selection receiving unit, from recommended data range setting information in which a recommended data range that is recommended as a range to be used for the input data is set, for each of the diagnostic assistance programs and outputs the acquired recommended data range; and a designated data range receiving unit that receives an input of a designated data range, which is designated as a range to be used for the input data, in the medical data after the recommended data range is output from the recommended data range output unit.

In the medical assistance device according to above aspect, it is preferable that the device further includes a screen generation unit that generates a medical data display screen to display the medical data, and the recommended data range output from the recommended data range output unit is displayed on the medical data display screen.

In the medical assistance device according to above aspect, it is preferable that the recommended data range includes an essential data range, which is essential as a range to be used for the input data, and an allowable data range, which is not essential as a range to be used for the input data but is allowed, and the essential data range and the allowable data range are displayed distinguishably on the medical data display screen.

In the medical assistance device according to above aspect, it is preferable that the medical data display screen has a function of designating the designated data range, and the designated data range receiving unit receives an input of the designated data range that is designated through the medical data display screen. In addition, the diagnostic assistance information may be displayed on the medical data display screen. It is preferable that the medical data display screen is a screen that is common to a plurality of diagnostic assistance programs.

In the medical assistance device according to above aspect, it is preferable that the device further includes a program control unit that controls the diagnostic assistance program.

In the medical assistance device according to above aspect, it is preferable that the device further includes a supplementary data output unit that, in a case where missing data that is data outside the designated data range and inside the recommended data range is present, outputs supplementary data to supplement the missing data, the program control unit executes the diagnostic assistance program using data, which is obtained by adding the supplementary data to the medical data of the designated data range, as the input data.

In the medical assistance device according to above aspect, the supplementary data is default data that is set in advance and is applicable in common to a plurality of the patients. Alternatively, the supplementary data may be estimated data that is estimated for each patient based on the medical data.

In the medical assistance device according to above aspect, it is preferable that the diagnostic assistance program used for each medical unit is registered in advance, the program selection receiving unit receives a selection of the medical unit as a selection of the diagnostic assistance program to be used, and the program control unit executes the diagnostic assistance program corresponding to the medical unit. The medical unit is at least one of the patient, a disease that the patient suffers, a department, a medical facility, an event that occurs in a course of treatment for the patient, a medical phase that is a progressive stage of treatment or disease, and a medical purpose.

In the medical assistance device according to above aspect, the medical data has a plurality of items, and at least one of the plurality of items is recorded in time series, and the designated data range is at least one of a range of the item determined by designation of the item and a period determined by designation of a temporal range.

According to another aspect of the invention, there is provided an operation method of a medical assistance device, including: a program selection reception step of receiving a selection of a diagnostic assistance program to be used among a plurality of diagnostic assistance programs that are executed to perform calculation using medical data of a patient as input data and output a result of the calculation as diagnostic assistance information for assisting diagnosis of the patient; a recommended data range output step of acquiring a recommended data range corresponding to the diagnostic assistance program received in the program selection reception step, from recommended data range setting information in which a recommended data range that is recommended as a range to be used for the input data is set, for each of the diagnostic assistance programs and outputting the acquired recommended data range; and a designated data range reception step of receiving an input of a designated data range, which is designated as a range to be used for the input data, in the medical data after the output of the recommended data range in the recommended data range output step, wherein all of the steps are performed.

According to still another aspect of the invention, there is provided a non-transitory computer-readable recording medium on which an operation program for a medical assistance device is recorded, wherein the program causes a computer to execute: a program selection reception function of receiving a selection of a diagnostic assistance program to be used among a plurality of diagnostic assistance programs that are executed to perform calculation using medical data of a patient as input data and output a result of the calculation as diagnostic assistance information for assisting diagnosis of the patient; a recommended data range output function of acquiring a recommended data range corresponding to the diagnostic assistance program received through the program selection reception function, from recommended data range setting information in which a recommended data range that is recommended as a range to be used for the input data is set, for each of the diagnostic assistance programs and outputting the acquired recommended data range; and a designated data range reception function of receiving an input of a designated data range, which is designated as a range to be used for the input data, in the medical data after the output of the recommended data range through the recommended data range output function, wherein all of the functions are realized using the medical assistance device.

According to still another aspect of the invention, there is provided a medical assistance system, including: a medical assistance server; a client terminal; a network that communicably connects the medical assistance server and the client terminal to each other; and the medical assistance device.

In the medical assistance system according to above aspect, it is preferable that the system further includes a program control unit that controls the diagnostic assistance program; and a supplementary data output unit that, in a case where missing data that is data outside the designated data range and inside the recommended data range is present, outputs supplementary data to supplement the missing data, wherein the program control unit executes the diagnostic assistance program using data, which is obtained by adding the supplementary data to the medical data of the designated data range, as the input data.

In the medical assistance system according to above aspect, it is preferable that the program control unit and the supplementary data output unit are provided in the medical assistance server. Alternatively, the program control unit may be provided in the medical assistance server, and the supplementary data output unit is provided in the client terminal, and the medical assistance server may transmit the missing data to the client terminal, and the client terminal may transmit the supplementary data to the medical assistance server.

In the medical assistance system according to above aspect, the recommended data range output unit is, for example, provided in the medical assistance server, and reads the recommended data range from a storage unit that stores the recommended data range. Alternatively, the recommended data range output unit is provided in the client terminal, and receives the recommended data range that is transmitted from a storage unit of the medical assistance server that stores the recommended data range.

According to the invention, since the recommended data range that is recommended as a range of input data calculated by the diagnostic assistance program is output, it is possible to assist the range designation of the user. As a result, it is possible to provide a medical assistance device capable of improving work efficiency by reducing the burden on a user, an operation method of a medical assistance device, a non-transitory computer-readable recording medium, and a medical assistance system.

BRIEF DESCRIPTION OF THE DRAWINGS

FIG. 8 is a diagram showing the content of a disease-specific list.

FIG. 12 is a diagram showing the content of a recommended data range list.

FIG. 16 is a diagram showing the content of a recommended data range list in a second embodiment.

FIG. 21 is a diagram showing the content of a default data list.

DESCRIPTION OF THE PREFERRED EMBODIMENTS

First Embodiment

Figure 1:
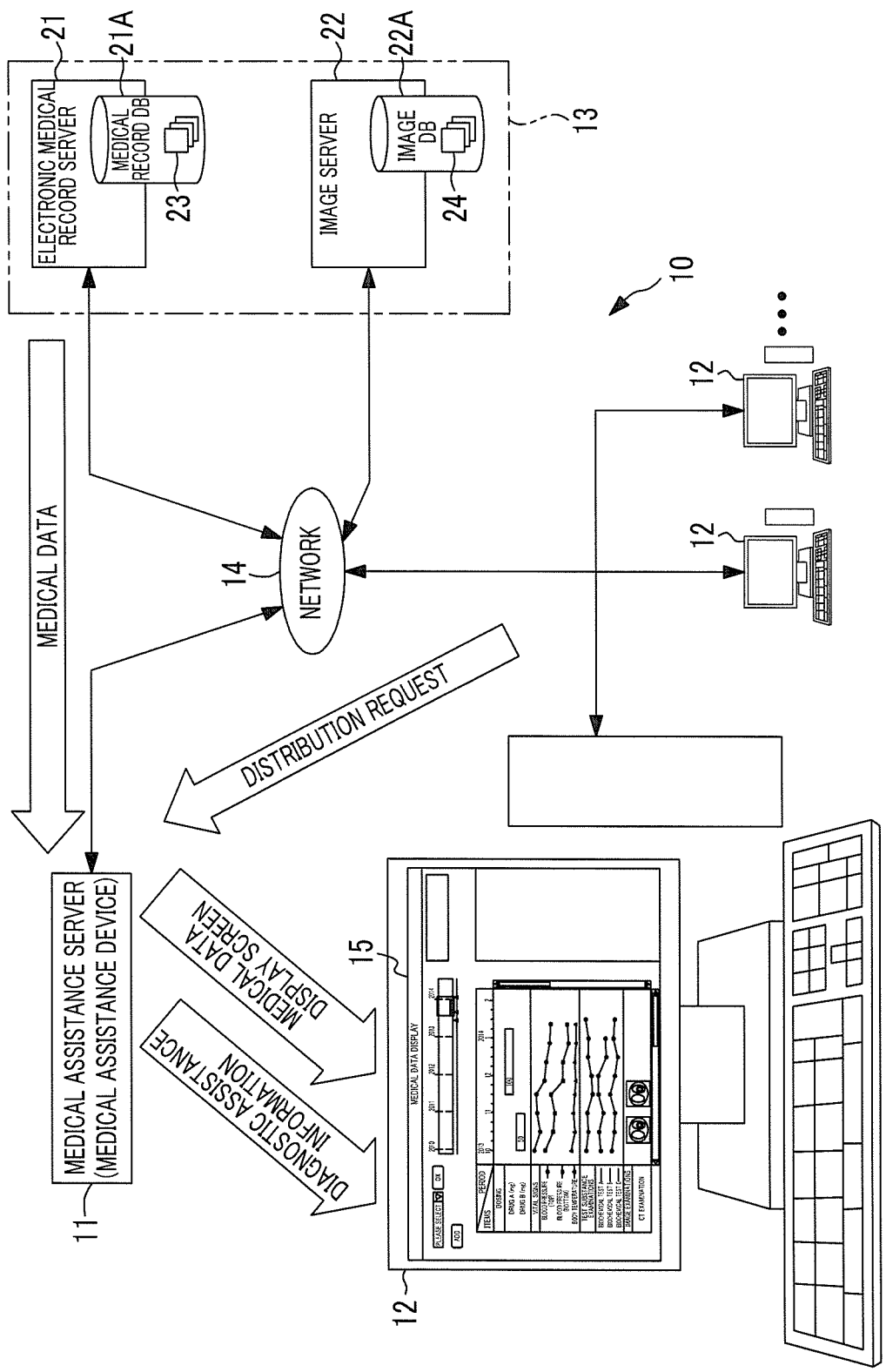
FIG. 1 is an explanatory diagram showing a medical assistance system.

In FIG. 1, a medical assistance system 10 is a computer system for managing and using medical information in a medical facility, such as a hospital. The medical assistance system 10 includes a medical assistance server 11, a client terminal 12, and a server group 13. These are communicably connected to each other through a network 14, such as a local area network (LAN) provided in the medical facility.

The medical assistance server 11 functions as a medical assistance device of the invention. Specifically, the medical assistance server 11 receives a distribution request from the client terminal 12. In response to the received distribution request, the medical assistance server 11 transmits a request for acquisition of medical data, which has been acquired in the entire course of treatment for the patient, to the server group 13. The medical assistance server 11 acquires the medical data transmitted from the server group 13 in response to the acquisition request, and generates a medical data display screen 15 (refer to FIG. 6 or the like) based on the acquired medical data. The medical assistance server 11 transmits the generated medical data display screen 15 to the client terminal 12 that has made the distribution request.

In addition, the medical assistance server 11 has a function of using a plurality of diagnostic assistance programs 101 (refer to FIG. 13), and outputs diagnostic assistance information that is calculated by executing the diagnostic assistance programs 101 using the medical data as input data. The diagnostic assistance information is transmitted to the client terminal 12 by being superimposed on the medical data display screen 15 (refer to FIG. 11).

The client terminal 12 is installed in each department, such as internal medicine, surgery, otolaryngology, and ophthalmology, in the medical facility, and is operated by the doctor in each department that is a user. The client terminal 12 transmits a distribution request for medical data to the server group 13, and transmits a distribution request for the medical data display screen 15 to the medical assistance server 11. The client terminal 12 displays the medical data or the medical data display screen 15, which is transmitted from the server group 13 or the medical assistance server 11 in response to the distribution request, so that the doctor can see it. That is, the client terminal 12 functions as a viewer terminal for a doctor to view the medical data or the medical data display screen 15.

The medical assistance server 11 distributes the medical data display screen 15 to the client terminal 12, for example, in the form of XML data for web distribution created by a markup language, such as Extensible Markup Language (XML). The client terminal 12 reproduces and displays the medical data display screen 15 on the web browser based on the XML data.

The server group 13 searches for medical data corresponding to the distribution request from the client terminal 12, and transmits the searched medical data to the client terminal 12. In addition, the server group 13 searches for medical data corresponding to the acquisition request from the medical assistance server 11, and transmits the searched medical data to the medical assistance server 11.

The server group 13 includes an electronic medical record server 21 and an image server 22. The electronic medical record server 21 includes a medical record database (hereinafter, abbreviated as a DataBase (DB)) 21A in which an electronic medical record 23 is stored. In the electronic medical record 23, medical examination records data such as the content of interview or the diagnostic content, examination data such as examination values of medical examinations including test substance examinations (for example, a blood test and a biochemical test) and physiological tests (for example, electroencephalography), measurement data such as measurement values of vital signs (for example, patient's heart rate, pulse, blood pressure, and body temperature), and treatment records data such as treatment, surgery, and dosing are input as medical data. These various kinds of data of the electronic medical record 23 can be input to the client terminal 12, and the electronic medical record 23 can be viewed at the client terminal 12.

The image server 22 is a so-called picture archiving and communication system (PACS) server, and has an image DB 22A in which an examination image 24 is stored. The examination image 24 is an image obtained by various image examinations, such as a computed tomography (CT) examination, a magnetic resonance imaging (MRI) examination, a simple X-ray examination, an ultrasonic examination, and an endoscopic examination. For example, the examination image 24 is created in the data file format of digital imaging and communications in medicine (DICOM) standards. The examination image 24 can be viewed at the client terminal 12.

Figure 2:
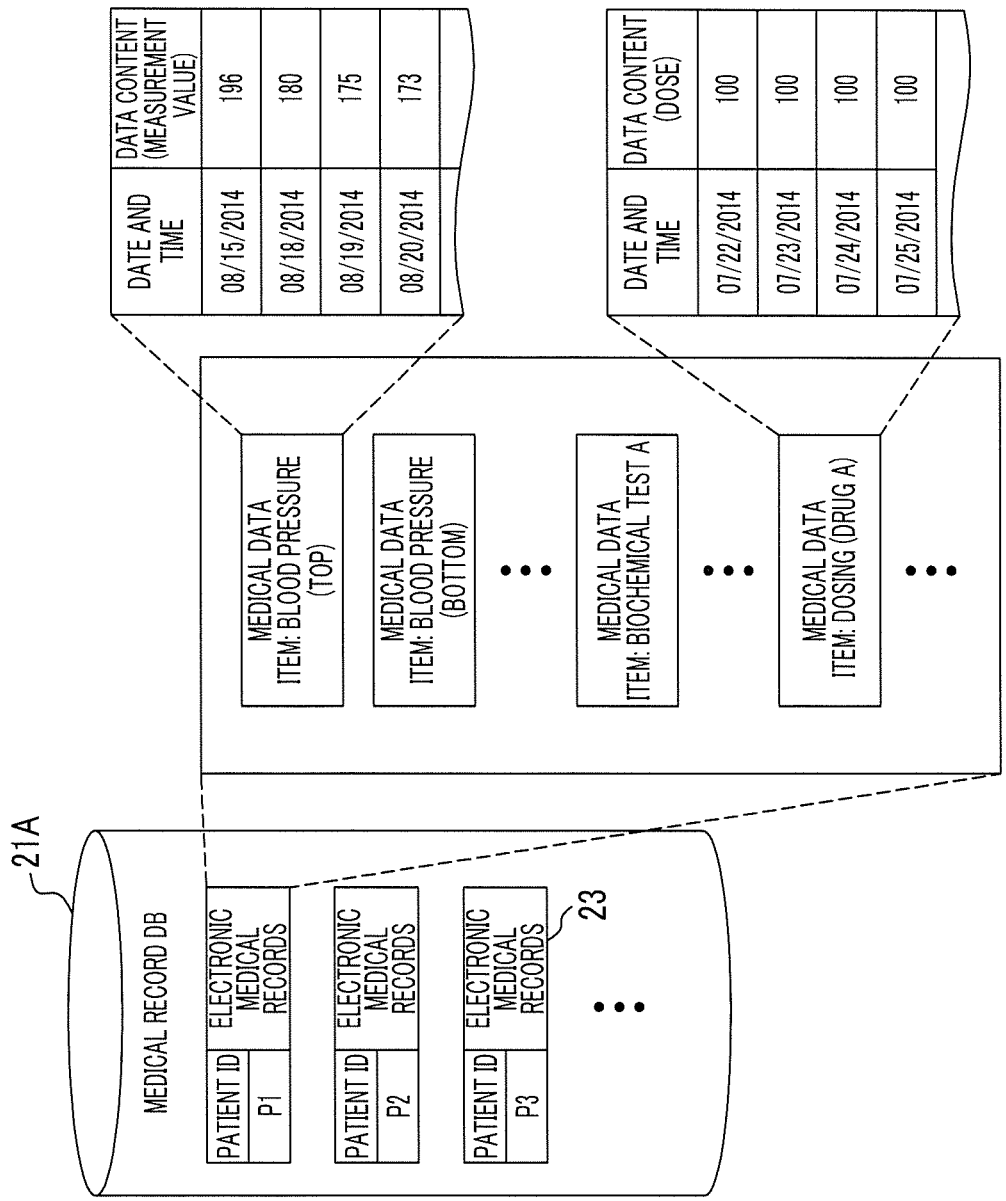
FIG. 2 is a diagram showing the content of electronic medical records stored in a medical record DB.
Figure 3:
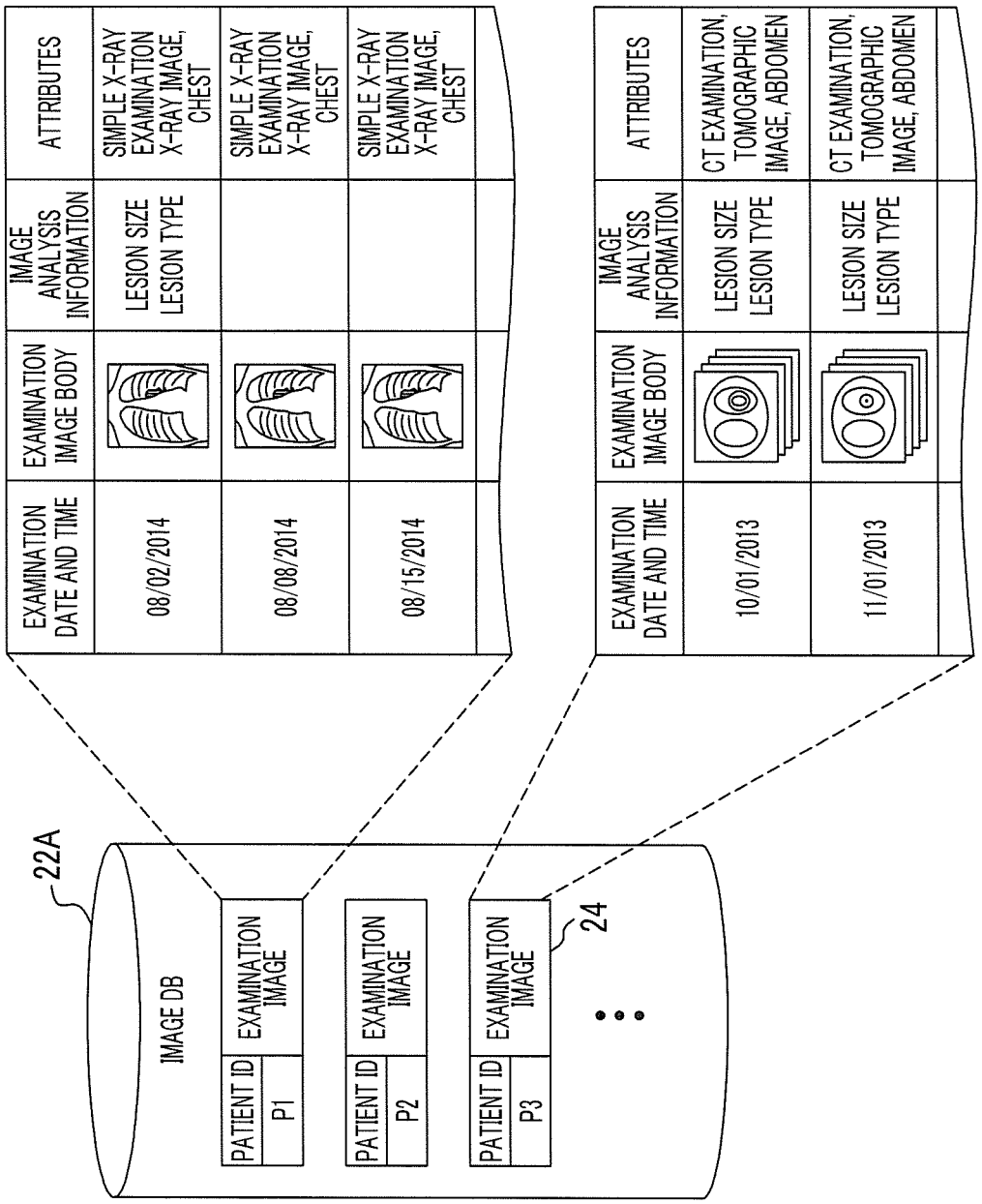
FIG. 3 is a diagram showing the content of an examination image stored in an image DB.

In the electronic medical record 23 and the examination image 24, patient identification data (ID) that is a number for identifying an individual patient or the like is stored as supplementary information so as to be associated therewith (refer to FIGS. 2 and 3). In the electronic medical record 23 and the examination image 24, searching from the DB 21A and DB 22A can be performed by using the supplementary information, such as a patient ID, as a search keyword.

In addition to the servers 21 and 22, the server group 13 may also include various servers, such as a health management information server for handling health management information that the patient measures daily using a blood pressure measuring instrument, a weighing scale, or the like at home and a genetic test information server for handling genetic test information that is a result of a genetic test of a patient. In recent years, it has become possible to mail a genetic test kit and a test result to patients. Therefore, since the patients themselves can easily perform genetic tests at home, it is expected that the genetic test will be more widespread in the future.

In FIG. 2, the electronic medical record 23 stored in the medical record DB 21A is managed in units of a patient by being associated with patient IDs, such as P1, P2, P3, . . . . Not only the patient ID but also the basic information (not shown) of the patient, such as the patient's name, sex, date of birth or age, address, and telephone number, and medical data of a plurality of items are recorded in the electronic medical record 23. Medical data is arranged in items, such as "blood pressure (top)", "blood pressure (bottom)", "biochemical test A", and "dosing (drug A)", and is recorded in time series. Although not shown in FIG. 2, the medical data includes not only the above-described medical examination records data such as the content of interview or the diagnostic content, measurement values of vital signs (for example, a heart rate, a pulse, and body temperature other than the blood pressure), and dosing but also treatment records data such as treatment or surgery. When there is a health management information server or a genetic test information server, health management information or genetic test information that is obtained from these servers and is recorded in the electronic medical record 23 is also included in the medical data.

The record of one case of each item of medical data includes information regarding the date and time, such as visit date and time, examination date and time, measurement date and time, and dosing date and time (date and time when medication was performed or prescription date and time), and the data content, such as the content of interview, the diagnostic content, examination values, measurement values, and dose. When the item is dosing, it may take time until the dosing effect appears. Accordingly, dosing over a predetermined period of time may be instructed by one prescription, for example, "take a predetermined amount per day continuously for 5 days". In this case, date and time for which the taking of the medicine is scheduled is recorded as the dosing date and time.

In FIG. 3, the examination image 24 stored in the image DB 22A is managed in units of a patient by being associated with a patient ID, similar to the electronic medical record 23. Not only the patient ID but also the attributes of each examination image, such as examination date and time when an image examination was performed, image analysis information, type of image examination (for example, "X-ray examination" or "CT examination"), type of each examination image ("X-ray image" or "tomographic image"), and an imaging part (for example, "chest" or "abdomen"), are associated with the examination image 24, as supplementary information. The type of image examination is used as an item of medical data. The image server 22 transmits the examination image 24 to the medical assistance server 11 or the client terminal 12, as medical data, together with the supplementary information, such as the image analysis information or the attributes.

In a simple X-ray examination, one X-ray image is captured by one image examination in many cases. However, as a tomographic image acquired by the CT examination, a plurality of examination images 24 may be captured by one image examination. Thus, when a plurality of examination images 24 are captured by one image examination, a common ID is assigned to each examination image 24 in order to indicate that the plurality of examination images 24 have been obtained by one image examination, and the plurality of examination images 24 are collectively managed as one examination image 24. This is the same for a case in which a plurality of examination images 24 are captured by a simple X-ray examination.

The image analysis information is information regarding the size, type, and the like of a lesion in the examination image 24. When the image examination is an ultrasonic examination, a blood flow measurement value obtained by analyzing the ultrasonic image is also included in the image analysis information. The image analysis information is a kind of diagnostic assistance information obtained by the image analysis using the diagnostic assistance program 101, for example. Alternatively, a result obtained when a doctor reads and determines the examination image 24 in the client terminal 12 may be input as the image analysis information.

The medical assistance server 11, the client terminal 12, and the servers 21 and 22 of the server group 13 are formed by installing a control program, such as an operating system, or an application program, such as a server program or a client program, into a computer as a base, such as a server computer, a personal computer, or a workstation.

Figure 4:
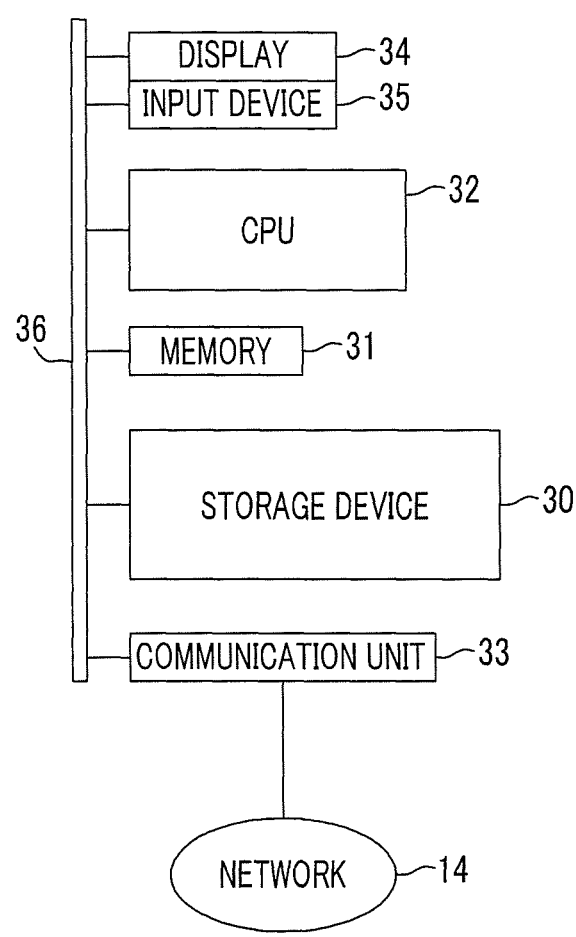
FIG. 4 is a block diagram showing the configuration of a computer that forms a medical assistance server or a client terminal.

In FIG. 4, the basic configurations of computers that configure the medical assistance server 11, the client terminal 12, and the like are the same, and each computer includes a storage device 30, a memory 31, a central processing unit (CPU) 32, a communication unit 33, a display 34, and an input device 35. These are connected to each other through a data bus 36.

The storage device 30 is a hard disk drive, which is built in a computer that forms the medical assistance server 11 or the client terminal 12 or which is connected to the computer through a cable or a network, or a disk array formed by connecting a plurality of hard disk drives. A control program such as an operating system, various application programs, and display data of various operation screens associated with these programs are stored in the storage device 30.

The memory 31 is a work memory required when the CPU 32 executes processing. The CPU 32 performs overall control of each unit of the computer by loading a program stored in the storage device 30 to the memory 31 and executing the processing according to the program.

The communication unit 33 is a network interface to perform transmission control of various kinds of information through the network 14. The display 34 displays various operation screens corresponding to the operation of the input device 35, such as a mouse or a keyboard. The operation screen has an operation function based on the graphical user interface (GUI). Each computer that forms the medical assistance server 11 or the client terminal 12 receives an input of an operation instruction from the input device 35 through the operation screen. In the following explanation, for the sake of distinction, a suffix "A" is attached to the reference numeral of each unit of the computer that forms the medical assistance server 11, and a suffix "B" is attached to the reference numeral of each unit of the computer that forms the client terminal 12.

An application program, such as electronic medical record software for viewing or editing the electronic medical record 23, image viewing software for viewing the examination image 24, or viewer software for viewing the medical data display screen 15, is installed in the client terminal 12.

Figure 5:
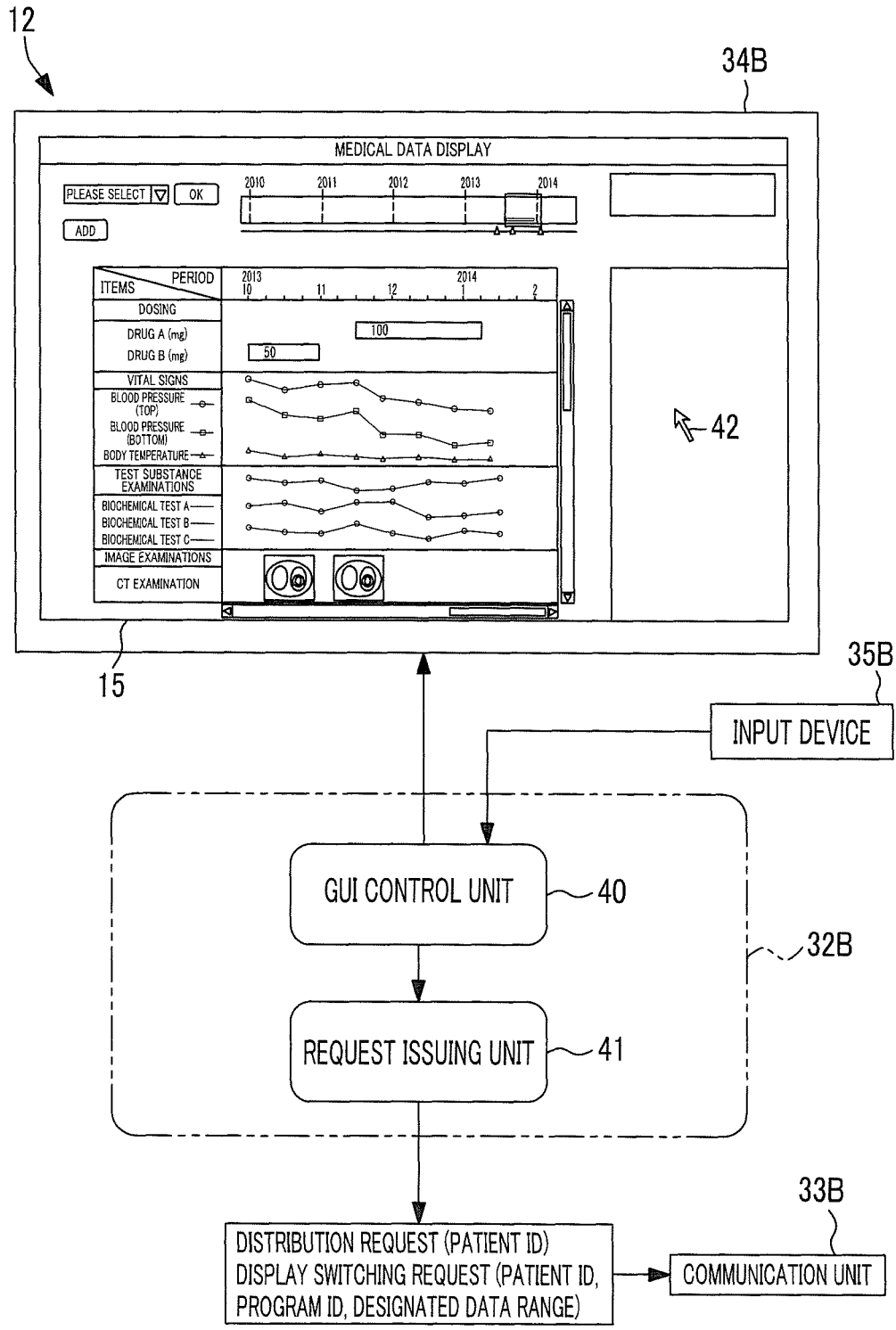
FIG. 5 is a block diagram showing a client terminal.

In FIG. 5, when the viewer software of the medical data display screen 15 is started, the CPU 32B of the client terminal 12 cooperates with the memory 31B to function as a GUI control unit 40 and a request issuing unit 41. The GUI control unit 40 displays the medical data display screen 15 transmitted from the medical assistance server 11 on the web browser of the display 34B. The GUI control unit 40 performs screen control according to an operation instruction that is input from the input device 35B through the medical data display screen 15, such as a button clicking operation using a cursor 42.

The request issuing unit 41 issues various requests to the medical assistance server 11, according to the operation instruction of the input device 35B given through the GUI control unit 40, to the communication unit 33B. The various requests include a distribution request for the medical data display screen 15 and a display switching request for the medical data display screen 15. The distribution request includes a patient ID. The patient ID is input through the startup screen of the viewer software, for example.

The display switching request is a process of requesting the medical assistance server 11 to switch the display content of the medical data display screen 15 according to the display switching instruction of the medical data display screen 15 using the input device 35B. There are three types of display switching requests. One includes a disease ID corresponding to the selection of a disease, another one includes a program ID corresponding to the selection of the diagnostic assistance program 101, and the last one includes a designated data range, which is designated by the doctor as a range to be used for the input data of the diagnostic assistance program 101.

The disease ID is a number for identifying each disease, such as lung cancer or a gastric ulcer. The program ID is a number for identifying each diagnostic assistance program 101. The designated data range includes a designated data item, which is determined by the designation of each item of medical data, and a designated data time, which is determined by the designation of a temporal range, as will be described later.

Figure 6:
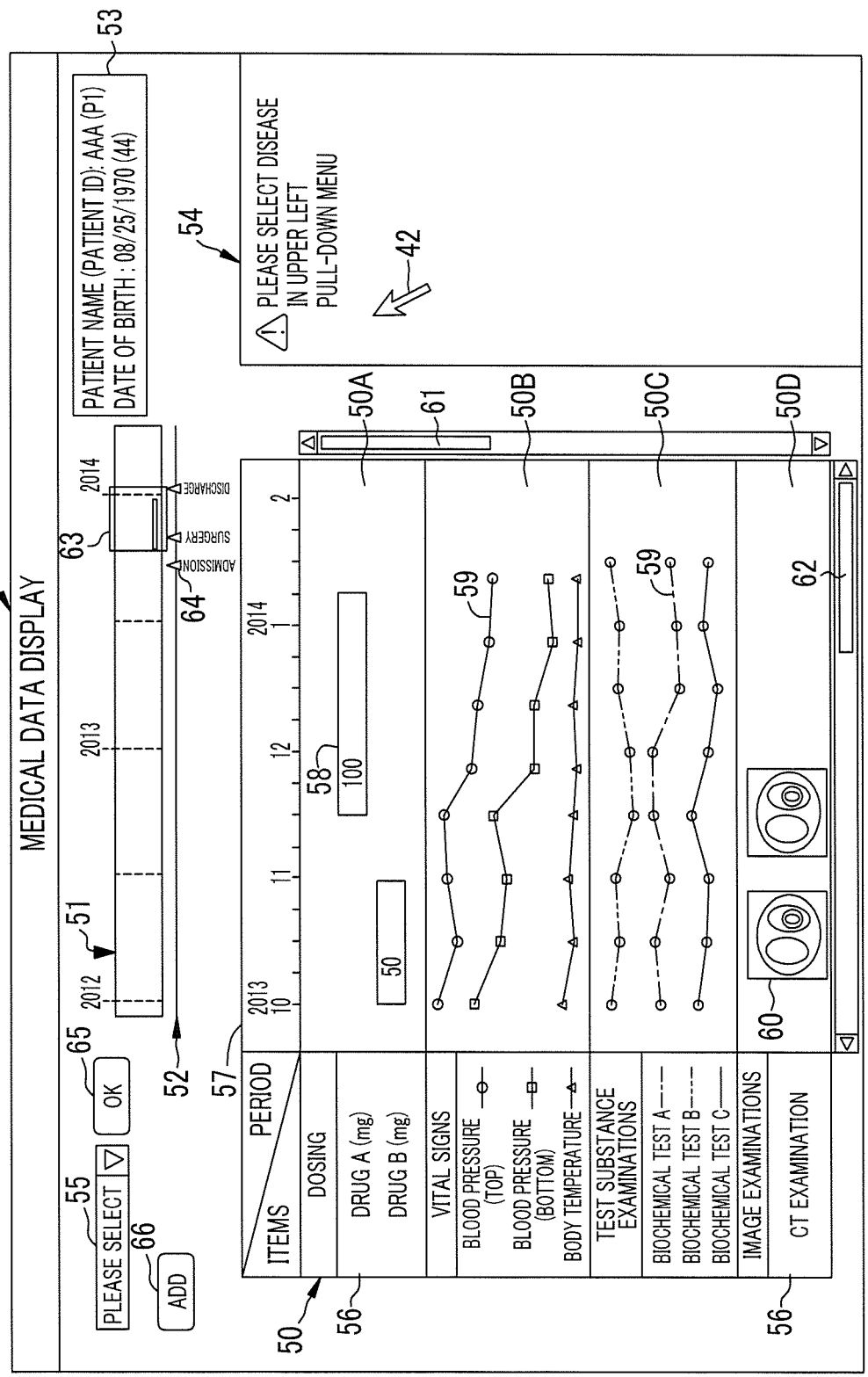
FIG. 6 is a diagram showing a medical data display screen.

In FIG. 6, the medical data display screen 15 includes a medical data display region 50, a period display region 51, an event display region 52, a patient information display region 53, a various information display region 54, and a pull-down menu 55.

In the medical data display region 50, the vertical axis indicates an item of medical data, and the horizontal axis indicates time. An item display column 56 is provided on the left, and a period display column 57 is provided on the top. In the item display column 56, major category names of items of medical data, such as "dosing", "vital signs", "test substance examinations", and "image examinations", and names of items such as "drug A, drug B", "blood pressure (top), blood pressure (bottom), body temperature", "biochemical test A, biochemical test B, biochemical test C", and "CT examination" are displayed. The period display column 57 shows a period for which medical data displayed in the medical data display region 50, of the medical data in the entire course of treatment for the patient, has been acquired (hereinafter, referred to as a first period). In the period display column 57, markings and information, such as year, month, and day, are arranged according to the set time scale. In FIG. 6, the first period is approximately three and a half months from October, 2013 to mid-January, 2014.

The medical data display region 50 is divided into a plurality of sub-regions 50A, 50B, 50C, 50D, . . . in the vertical direction by a plurality of item display columns 56. Major category names of items of "dosing", "vital signs", "test substance examinations", and "image examinations" are assigned to the sub-regions 50A, 50B, 50C, and 50D, respectively. In the sub-region 50A, start and end dates of dosing in the first period and a bar 58 indicating a dose are displayed. The inside of the parentheses of the item display column 56 of "dosing" indicates a unit of the dose displayed on the bar 58. In the sub-regions 50B and 50C, a line graph 59 obtained by plotting the measured values of vital signs or the examination values of test substance examinations in the first period and connecting these values in lines is displayed. In the item display columns 56 of "vital signs" and "test substance examinations", the legend of the line graph 59 is displayed. In the sub-region 50D, a thumbnail image 60 of the examination image 24 obtained in the first period is displayed. The bar 58, the plot of measured values or examination values forming the line graph 59, and the thumbnail image 60 are disposed at positions corresponding to the dosing date and time, measurement date and time, and examination date and time.

The medical data display region 50 can be vertically and horizontally scrolled by scroll bars 61 and 62. By operating the scroll bar 61 for scrolling in the vertical direction, it is possible to change the display ranges of the item display column 56 and the sub-regions. In addition, by operating the scroll bar 62 for scrolling in the horizontal direction, it is possible to change the display range of the first period.

The period display region 51 is a region where a period with a relatively longer time scale (hereinafter, referred to as a second period) than the first period shown in the period display column 57 is displayed. In the period display region 51, information of the year and the scale of each year are displayed, and a period indicator 63 is provided. The period indicator 63 shows to which part of the second period the first period corresponds. The width of the period indicator 63 corresponds to the width of the first period in the time scale of the second period. Since the first period is approximately three and a half months in FIG. 6, the width of the period indicator 63 corresponds to the width of three and a half months in the time scale of the second period.

The period indicator 63 moves the period display region 51 in the horizontal direction in conjunction with the operation of the scroll bar 62. It is also possible to change the display range of the first period by moving the period indicator 63 itself in the horizontal direction or changing the width of the period indicator 63. The first period to be first displayed may be a period before a predetermined period from the acquisition of the latest medical data, or may be designated when a doctor inputs a patient ID on the startup screen.

The event display region 52 shows the date and time when the event in the course of treatment for the patient has occurred, such as admission and discharge dates or a surgery date, together with an arrow 64 for the event name and the period display region 51. Basic information, such as the patient name of a patient of a patient ID input on the startup screen of the viewer software, the patient ID, and the date of birth, is displayed in the patient information display region 53.

In the various information display region 54, various kinds of information to be communicated to the doctor are displayed. In the example shown in FIG. 6, a message prompting the selection of a disease in the pull-down menu 55 is displayed in the various information display region 54.

The pull-down menu 55 is a display for selecting a disease. In the pull-down menu 55, the names of all diseases, such as "disease A" and "disease B" (refer to FIG. 8), are displayed as options. An OK button 65 is provided next to the pull-down menu 55, and an add button 66 is provided below the pull-down menu 55. By clicking the add button 66 with the cursor 42, it is possible to newly add the pull-down menu 55. Therefore, it is possible to select a complex disease, such as a "complex disease AB" (refer to FIG. 8). Complex diseases are more common in the elderly. As aging becomes faster in recent years, the number of patients suffering from complex diseases is also increasing. For this reason, such a function is effective.

When a disease is selected by operating the pull-down menu 55 with the cursor 42 and the OK button 65 is clicked, a display switching request including the disease ID of the selected disease is transmitted from the client terminal 12 to the medical assistance server 11. It is possible to provide a search bar for searching for a candidate for the disease, which is predicted from the symptoms, with the symptoms of the patient as a search keyword.

Figure 7:
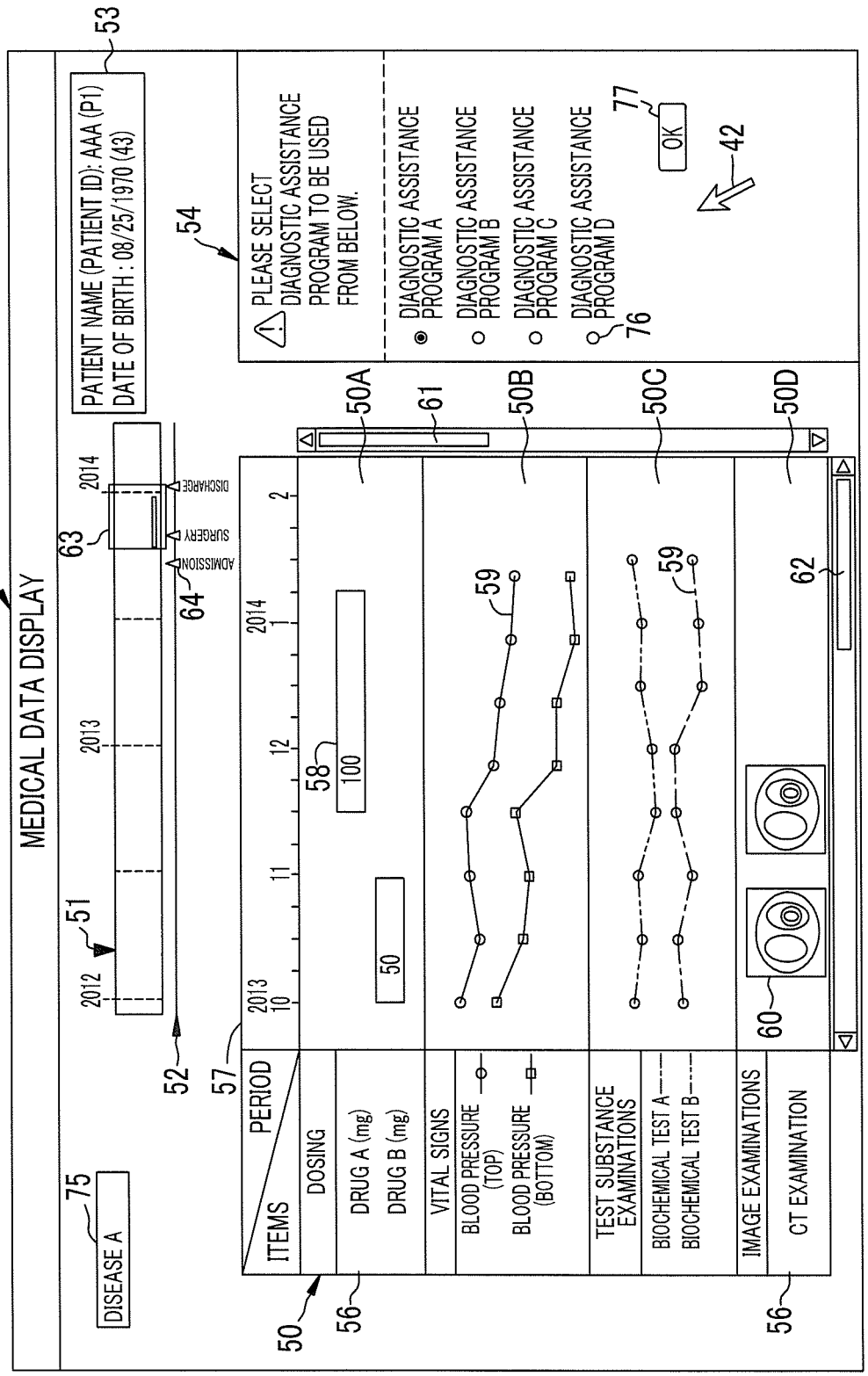
FIG. 7 is a diagram showing a medical data display screen for receiving the selection of a diagnostic assistance program to be used.

In response to the display switching request including the disease ID, the display of the medical data display screen 15 is switched as shown in FIG. 7. FIG. 7 is an example when the "disease A" is selected in the pull-down menu 55. The display content of the medical data display screen 15 shown in FIG. 7 is basically the same as that of the medical data display screen 15 shown in FIG. 6, but is different in that the items of the medical data displayed in the medical data display region 50 have been changed. FIG. 7 shows a state in which the line graphs 59 regarding the "body temperature" and the "biochemical test C" displayed in FIG. 6 have been removed.

The switching of the items of the medical data is performed based on a disease-specific list 80 shown in FIG. 8. In FIG. 8, the disease-specific list 80 is a list obtained by recording the item (hereinafter, referred to as a display item) of medical data displayed on the medical data display screen 15 and the diagnostic assistance program 101 so as to be associated with each other for each type of disease, such as the disease A and the disease B. For example, for the "disease A", items of "drug A, drug B", "blood pressure (top), blood pressure (bottom)", "biochemical test A, biochemical test B", and "CT examination" are registered as display items, and a plurality of "diagnostic assistance programs (PR1), (PR2), . . . " are registered as the diagnostic assistance programs 101. In addition, for the "complex diseases AB" in which the "disease A" and the "disease B" are combined, items of "drug A, drug B, drug C", "blood pressure (top), blood pressure (bottom)", "biochemical test A, biochemical test B, biochemical test F, biochemical test G", "blood test E", "CT examination", and "ultrasonic examination" are registered as display items, and diagnostic assistance programs (PR100), . . . are registered as the diagnostic assistance programs 101.

Figure 13:
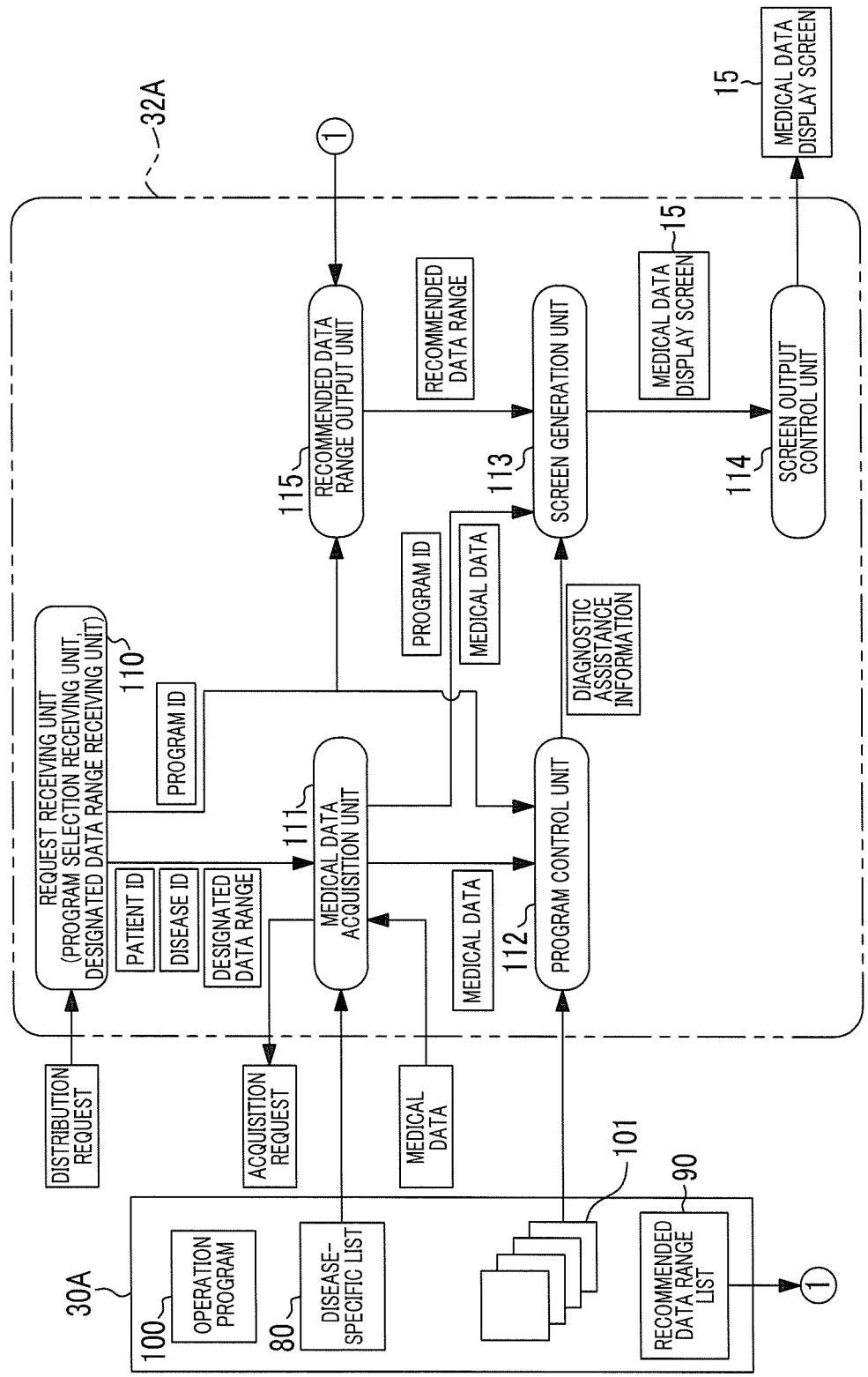
FIG. 13 is a block diagram showing functional units of a CPU of a medical assistance server and the flow of various kinds of information.

The disease-specific list 80 is stored in the storage device 30A of the medical assistance server 11 (refer to FIG. 13). The display items and the diagnostic assistance program 101 of the disease-specific list 80 are registered in advance by the administrator of the medical assistance server 11 or the doctor who operates the client terminal 12. The display items and the diagnostic assistance program 101 of the disease-specific list 80 can be updated when necessary. In addition, "D1", "D1+D2", and the like in the parentheses after the disease indicate disease IDs. In addition, "PR1", "PR20", "PR100", and the like in the parentheses after the diagnostic assistance program 101 indicate program IDs.

In FIG. 7, on the medical data display screen 15, a disease display region 75 is provided instead of the pull-down menu 55, the OK button 65, and the add button 66 in FIG. 6. In the disease display region 75, the name (in this example, "disease A") of the disease selected in the pull-down menu 55 is displayed.

In addition, a message prompting the selection of the diagnostic assistance program 101 to be used is displayed in the various information display region 54. In the various information display region 54, the names of the diagnostic assistance programs 101 set in the disease-specific list 80 are listed, and a radio button 76 for selecting one diagnostic assistance program 101 among the displayed diagnostic assistance programs 101 and an OK button 77 are displayed.

FIG. 7 shows a state in which a "diagnostic assistance program A" is selected as the diagnostic assistance program 101 to be used by the radio button 76. When the desired diagnostic assistance program 101 is selected by the radio button 76 and the OK button 77 is clicked on the medical data display screen 15 shown in FIG. 7, a display switching request including the program ID of the diagnostic assistance program 101 selected by the radio button 76 is transmitted from the client terminal 12 to the medical assistance server 11.

Instead of or in addition to displaying the name of the diagnostic assistance program 101 in the various information display region 54, the intended use of each diagnostic assistance program 101 may be displayed in the various information display region 54. The intended use indicates for which purpose the diagnostic assistance program 101 has been created. For example, "lesion measurement" is displayed as the intended use in the case of the diagnostic assistance program 101 for measuring the lesion size, and "side effects detection" is displayed as the intended use in the case of the diagnostic assistance program 101 for detecting the side effects of the drug.

Figure 9:
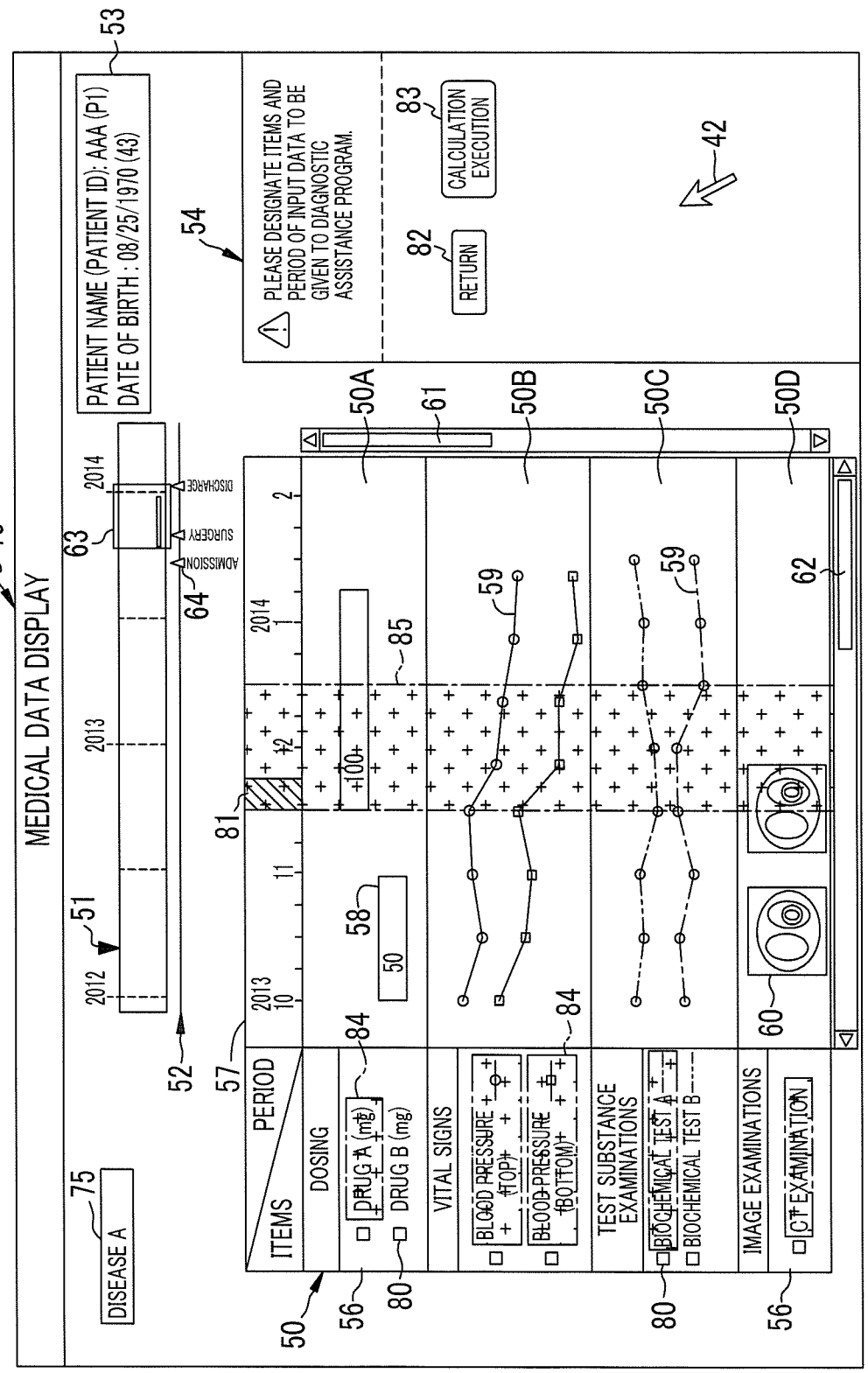
FIG. 9 is a diagram showing a medical data display screen which has a function of designating a range and on which a recommended data range is displayed.

In response to the display switching request including the program ID, the display of the medical data display screen 15 is switched as shown in FIG. 9. The medical data display screen 15 shown in FIG. 9 is basically the same display content as the medical data display screen 15 shown in FIG. 7, but is different in that the function of designating a designated data range appears and the recommended data range is displayed.

Specifically, the function of inputting the designated data range is realized by a check box 80 for designating each item in the input data, which is provided in the item display column 56, and a period designating bar 81 (indicated by hatching of oblique lines) for designating the period of the input data, which is provided in the period display column 57. The item designated through the check box 80 is a designated data item, and the period designated through the period designating bar 81 is a designated data period.

The recommended data range is a range that is set by the development company of the diagnostic assistance program 101 in advance and is recommended for the range of medical data to be used for the input data of the diagnostic assistance program 101. The recommended data range includes a recommended data item and a recommended data period. The recommended data item is an item that corresponds to the designated data item and is recommended as an item to be used for the input data among the items of medical data. The recommended data period is a period that corresponds to the designated data period and is recommended as a period to be used for the input data among the pieces of medical data in the entire course of treatment for the patient.

In FIG. 9, among the items of the item display column 56, an item highlighted with a different color (for example, pink fluorescent color when the color of the background is gray) from the background of the item display column 56, as surrounded by the one-dot chain line given with reference numeral 84 and shown by cross hatching, is a recommended data item. In addition, a period highlighted with a different color (for example, pink fluorescent color when the color of the background is gray) from the background, as surrounded by the one-dot chain line given with reference numeral 85 and shown by cross hatching, is a recommended data period. In FIG. 9, "drug A", "blood pressure (top), blood pressure (bottom), "biochemical test A", and "CT examination" are displayed as the recommended data items, and "one month from the dosing date of drug A" is displayed as the recommended data period. That is, the medical data display screen 15 also serves as a recommended data range display screen.

A message prompting the designation of items and a period of input data, a return button 82 for returning the medical data display screen 15 to the state shown in FIG. 7, and the calculation execution button 83 are displayed in the various information display region 54.

Figure 10:
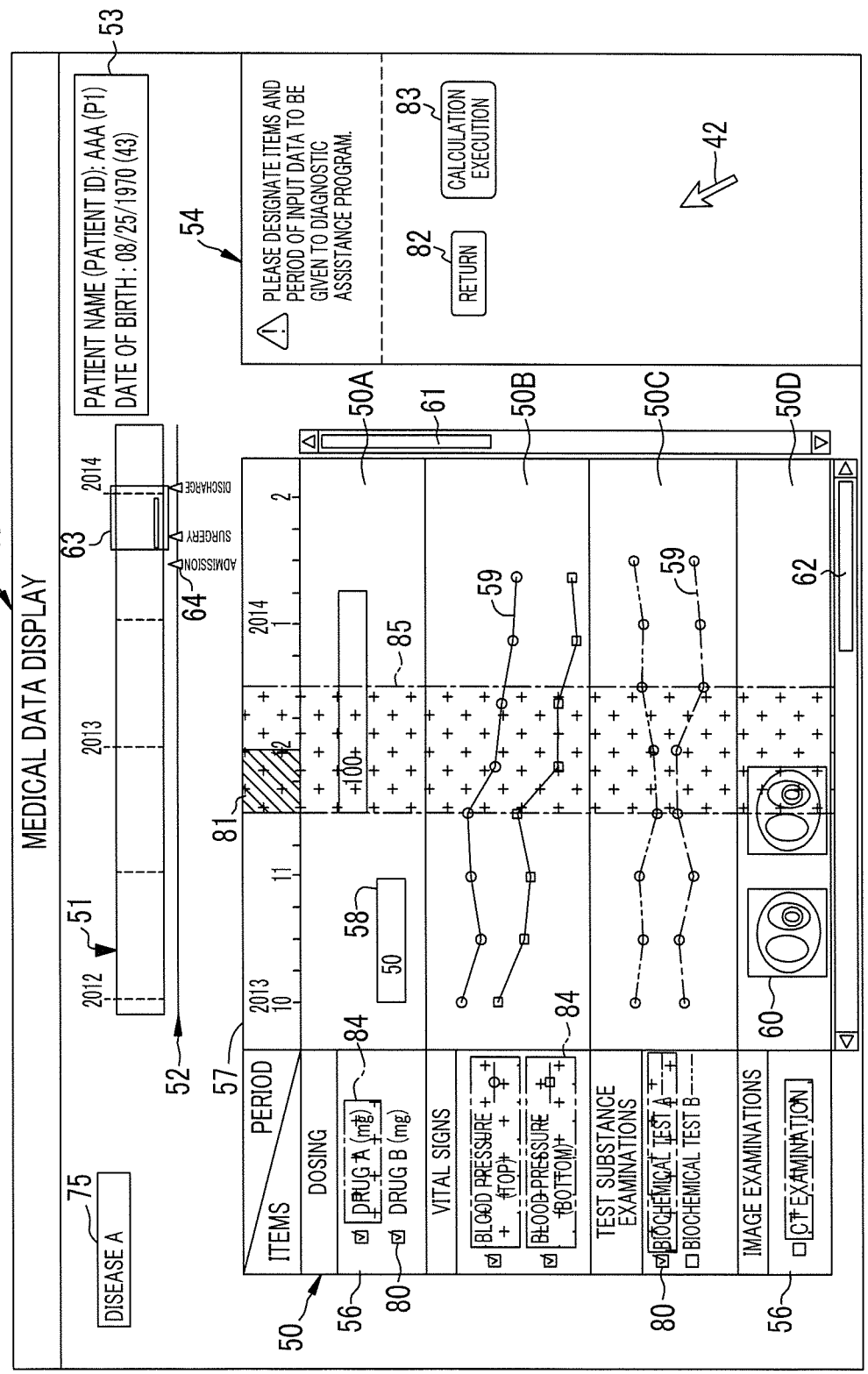
FIG. 10 is a diagram showing a state in which an item and a period have been designated on the medical data display screen.

As shown in FIG. 10, when the check box 80 of a desired item is designated by the cursor 42, the width of the period designating bar 81 is set to a desired period, and the calculation execution button 83 is clicked, a display switching request including a designated data range, which includes the item designated by the check box 80 as a designated data item and the period designated by the period designating bar 81 as a designated data period, is transmitted from the client terminal 12 to the medical assistance server 11. In FIG. 10, as shown by a check mark in the check box 80, a state is shown in which "drug A, drug B", "blood pressure (top), blood pressure (bottom)", and "biochemical test A" are designated as designated data items and two weeks of the third and fourth weeks in November, 2013 are designated as a designated data period. As the period designated by the period designating bar 81, it is possible to mention not only a predetermined period from the start of dosing of certain drugs illustrated in FIG. 10 but also a predetermined period from the date on which an event of surgery or the like occurs and a period for which the user wants to see a change in the lesion of cancer or the like.

Figure 11:
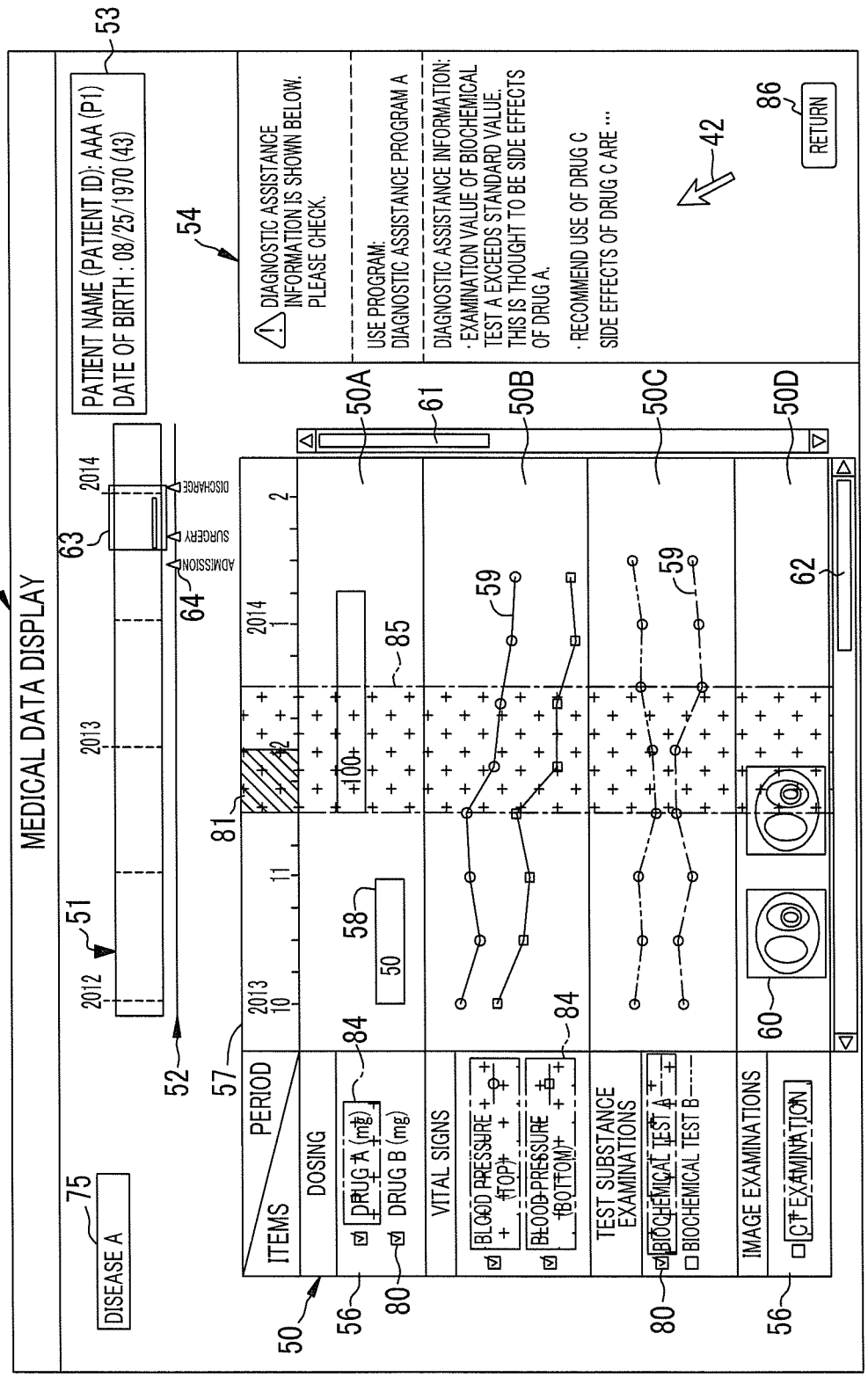
FIG. 11 is a diagram showing a medical data display screen on which diagnostic assistance information is displayed.

In response to the display switching request including a designated data range, the display of the medical data display screen 15 is switched as shown in FIG. 11. The display content of the medical data display screen 15 shown in FIG. 11 is basically the same as that of the medical data display screen 15 shown in FIG. 10, but the content displayed in the various information display region 54 is different. Specifically, a message prompting the confirmation of diagnostic assistance information, the name of the used diagnostic assistance program 101, diagnostic assistance information, and a return button 86 for returning the display to the state shown in FIG. 10 are displayed in the various information display region 54. In FIG. 11, findings about the examination value of "biochemical test A", comments that recommend the use of "drug C" other than "drugs A and B", and comments regarding the side effects of "drug C" are illustrated as diagnostic assistance information.

On the medical data display screen 15 shown in FIG. 11, a display 84 of recommended data items and a display 85 of a recommended data period and the designation state of designated data items and a designated data period using the check box 80 and the period designating bar 81 are displayed.

In FIG. 12, a recommended data range list 90 is a list in which recommended data items and a recommended data period, which form a recommended data range, are recorded for each diagnostic assistance program 101. The recommended data range list 90 corresponds to recommended data range setting information. For example, for the "diagnostic assistance program (PR1)", items of "drug A", "blood pressure (top), blood pressure (bottom), pulse, body temperature", and "biochemical test A" are registered as the recommended data items, and "one month from the dosing date of drug A" is registered as the recommended data period. The display 84 of the recommended data item and the display 85 of the recommended data period shown in FIG. 9 or the like are performed based on the recommended data range recorded in the recommended data range list 90. As the recommended data period, only a period, such as "one month or more", may be simply set without designating the specific date and time, such as the dosing date and time of the drug A in the example described above. In this case, for example, a minimum period required to execute the diagnostic assistance program 101 is set.

The recommended data range list 90 is stored in the storage device 30A of the medical assistance server 11 (refer to FIG. 13). That is, the storage device 30A corresponds to a storage unit.

The recommended data range is a range of input data for the output of the reliable diagnostic assistance information by the diagnostic assistance program 101.

In FIG. 13, an operation program 100 and a plurality of diagnostic assistance programs 101 are stored in the storage device 30A of the medical assistance server 11 as application programs. The operation program 100 is a program for operating a computer, which forms the medical assistance server 11, as a medical assistance device.

In addition to the various programs, the disease-specific list 80 shown in FIG. 8 and the recommended data range list 90 shown in FIG. 12 are stored in the storage device 30A.

When the operation program 100 starts, the CPU 32A of the medical assistance server 11 cooperates with the memory 31 to function as the request receiving unit 110, a medical data acquisition unit 111, a program control unit 112, a screen generation unit 113, a screen output control unit 114, and a recommended data range output unit 115.

The request receiving unit 110 has a request receiving function of receiving a distribution request and a display switching request transmitted from the client terminal 12. More specifically, the request receiving unit 110 receives a distribution request including a patient ID. In addition, the request receiving unit 110 receives a display switching request including a disease ID, a program ID, and a designated data range. That is, the request receiving unit 110 corresponds to a program selection receiving unit and a designated data range receiving unit. The request receiving unit 110 transmits a patient ID, a disease ID, and a designated data range to the medical data acquisition unit 111, and transmits a program ID to the program control unit 112 and the recommended data range output unit 115.

The medical data acquisition unit 111 has a medical data acquisition function of acquiring desired medical data.

When a patient ID from the request receiving unit 110 is received, the medical data acquisition unit 111 outputs an acquisition request having the patient ID as a search keyword to the communication unit 33A (not shown). In response to the acquisition request, medical data in the entire course of treatment for the patient, which is transmitted from the server group 13 and is received by the communication unit 33A, is acquired. The medical data acquisition unit 111 stores the acquired medical data in the storage device 30A, and transmits the acquired medical data to the screen generation unit 113.

When a disease ID from the request receiving unit 110 is received, the medical data acquisition unit 111 reads the program ID of the diagnostic assistance program 101 and a display item corresponding to the received disease ID from the disease-specific list 80. The medical data acquisition unit 111 extracts medical data corresponding to the display item read from the disease-specific list 80 from the medical data in the entire course of treatment for the patient, which is acquired in response to the acquisition request and is stored in the storage device 30A, and transmits the extracted medical data and the program ID read from the disease-specific list 80 to the screen generation unit 113.

When the designated data range from the request receiving unit 110 is received, the medical data acquisition unit 111 extracts medical data corresponding to the received designated data range from the medical data in the entire course of treatment for the patient, which is acquired in response to the acquisition request and is stored in the storage device 30A, and transmits the extracted medical data to the program control unit 112.

The program control unit 112 has a program control function of controlling the diagnostic assistance program 101. In other words, the diagnostic assistance program 101 is executed under the control of the program control unit 112.

When a program ID from the request receiving unit 110 is received, the program control unit 112 reads the diagnostic assistance program 101 corresponding to the received program ID from the plurality of diagnostic assistance programs 101 stored in the storage device 30A. The program control unit 112 executes the diagnostic assistance program 101 by giving the medical data of the designated data range received from the medical data acquisition unit 111, as input data, to the read diagnostic assistance program 101, and outputs diagnostic assistance information. The program control unit 112 transmits the diagnostic assistance information to the screen generation unit 113.

The diagnostic assistance information is information for assisting the diagnosis of a patient by a doctor. In addition to the image analysis information such as the size or type of a lesion in the examination image 24, findings about the examination value, and the presence or absence of side effects from dosing that have been described above, measurement values, a decrease in the examination value, an increase rate, and the like can be mentioned as examples of the diagnostic assistance information. In addition, the diagnostic assistance information may be any information useful for diagnosis, such as the presentation of recommended drugs based on genetic test information.

The screen generation unit 113 has a screen generation function of generating various operation screens, such as the medical data display screen 15. The screen generation unit 113 generates the medical data display screen 15 based on the medical data. In addition, the screen generation unit 113 switches the display of the medical data display screen 15 from FIG. 6 to FIG. 7, 9, or 11 in response to the display switching request. The screen generation unit 113 transmits the generated various operation screens, such as the medical data display screen 15, to the screen output control unit 114.

The screen output control unit 114 has a screen output control function of outputting the various operation screens received from the screen generation unit 113 to the communication unit 33A. The screen output control unit 114 outputs the medical data display screen 15 and information of the client terminal 12, which has sent the distribution request or the display switching request (for example, Internet protocol (IP) address of the client terminal 12), to the communication unit 33A.

The recommended data range output unit 115 has a recommended data range output function of acquiring and outputting a recommended data range in order to present it to a doctor. The recommended data range output unit 115 reads a recommended data range corresponding to the program ID, which is received from the request receiving unit 110, from the recommended data range list 90. The recommended data range output unit 115 transmits the read recommended data range to the screen generation unit 113.

Based on the recommended data range received from the recommended data range output unit 115, the screen generation unit 113 performs the display 84 of the recommended data item and the display 85 of the recommended data period on the medical data display screen 15 shown in FIG. 9 or the like. Thus, by performing the display 84 of the recommended data item and the display 85 of the recommended data period on the medical data display screen 15, the recommended data range is presented to the doctor.

Figure 14:
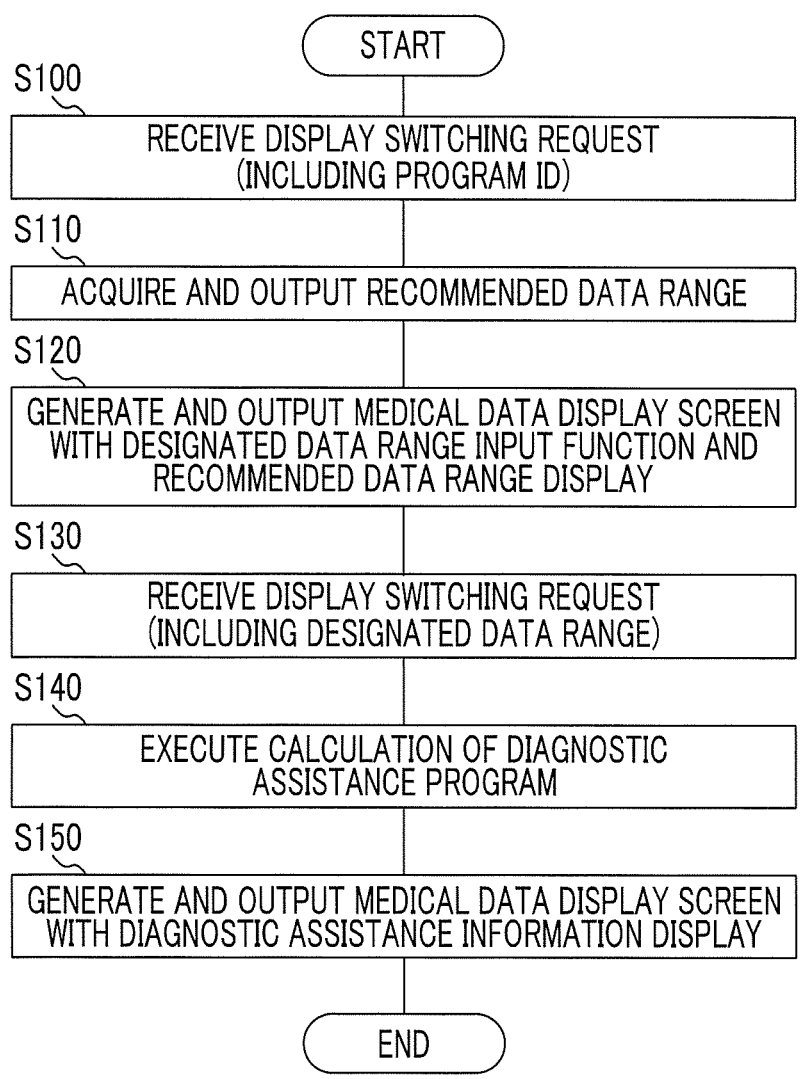
FIG. 14 is a flowchart showing the operation procedure of the functional units of the CPU of the medical assistance server.

Hereinafter, the operation of the above configuration will be described with reference to FIG. 14. First, the operation program 100 is started in the medical assistance server 11. Then, the request receiving unit 110, the medical data acquisition unit 111, the program control unit 112, the screen generation unit 113, the screen output control unit 114, and the recommended data range output unit 115 are built in the CPU 32A, and the computer that forms the medical assistance server 11 functions as a medical assistance device.

The doctor accesses the medical assistance server 11 on the web browser of the client terminal 12, and performs authorization for receiving the provision of medical assistance services by the medical assistance server 11. When authorization is performed, a startup screen for inputting a patient ID is displayed on the display 34B of the client terminal 12. The doctor inputs a patient ID of a patient whose medical data needs to be viewed on the startup screen. The patient ID input to the startup screen is transmitted from the client terminal 12 to the medical assistance server 11 as a distribution request.

In the medical assistance server 11, the distribution request from the client terminal 12 is received by the communication unit 33A. The distribution request is output to the request receiving unit 110 from the communication unit 33A, and is received by the request receiving unit 110. The patient ID of the distribution request is transmitted from the request receiving unit 110 to the medical data acquisition unit 111.

From the medical data acquisition unit 111, an acquisition request having the patient ID of the distribution request as a search keyword is output to the communication unit 33A. As a result, the acquisition request is transmitted from the communication unit 33A to the server group 13.

In response to the acquisition request from the medical assistance server 11, the server group 13 searches for the medical data in the entire course of treatment for the patient corresponding to the acquisition request. Then, the server group 13 transmits the searched medical data to the medical assistance server 11.

The medical data in the entire course of treatment for the patient from the server group 13 is received by the communication unit 33A, and is output to the medical data acquisition unit 111 from the communication unit 33A. Thus, the medical data in the entire course of treatment for the patient is acquired. The medical data is stored in the storage device 30A by the medical data acquisition unit 111, and is transmitted to the screen generation unit 113.

In the screen generation unit 113, the medical data display screen 15 shown in FIG. 6 is generated based on the medical data in the entire course of treatment for the patient from the medical data acquisition unit 111. Then, the medical data display screen 15 is output to the communication unit 33A by the screen output control unit 114. As a result, the medical data display screen 15 is transmitted from the communication unit 33A to the client terminal 12. In the client terminal 12, the medical data display screen 15 shown in FIG. 6 is displayed on the display 34B.

The doctor selects the disease of the patient in the pull-down menu 55 of the medical data display screen 15, and clicks the OK button 65. Then, a display switching request including the disease ID of the disease selected in the pull-down menu 55 is transmitted from the client terminal 12 to the medical assistance server 11.

In the medical assistance server 11, the display switching request from the client terminal 12 is received by the communication unit 33A. The display switching request is output to the request receiving unit 110 from the communication unit 33A, and is received by the request receiving unit 110. The disease ID of the display switching request is transmitted from the request receiving unit 110 to the medical data acquisition unit 111.

The medical data acquisition unit 111 reads, from the disease-specific list 80, the program ID of the diagnostic assistance program 101 and a display item corresponding to the disease ID of the display switching request. Then, medical data corresponding to the display item read from the disease-specific list 80 is extracted from the medical data in the entire course of treatment for the patient stored in the storage device 30A, and the extracted medical data and the program ID read from the disease-specific list 80 are transmitted to the screen generation unit 113.

In the screen generation unit 113, the medical data display screen 15 shown in FIG. 7 is generated based on the program ID and the medical data corresponding to the display item read from the disease-specific list 80 by the medical data acquisition unit 111. Then, the medical data display screen 15 is output to the communication unit 33A by the screen output control unit 114. As a result, the medical data display screen 15 is transmitted from the communication unit 33A to the client terminal 12. In the client terminal 12, the medical data display screen 15 shown in FIG. 7 is displayed on the display 34B.

The doctor selects the desired diagnostic assistance program 101 with the radio button 76 of the medical data display screen 15 shown in FIG. 7, and clicks the OK button 77. Then, a display switching request including the program ID of the diagnostic assistance program 101 selected by the radio button 76 is transmitted from the client terminal 12 to the medical assistance server 11.

In the medical assistance server 11, the display switching request from the client terminal 12 is received by the communication unit 33A. As shown in step S100 of FIG. 14, the display switching request is output to the request receiving unit 110 from the communication unit 33A, and is received by the request receiving unit 110. The program ID of the display switching request is transmitted from the request receiving unit 110 to the program control unit 112 and the recommended data range output unit 115.

The recommended data range output unit 115 reads a recommended data range corresponding to the program ID, which is received from the request receiving unit 110, from the recommended data range list 90, and outputs the recommended data range to the screen generation unit 113 (step S110).

The screen generation unit 113 generates the medical data display screen 15 shown in FIG. 9 based on the recommended data range from the recommended data range output unit 115. Then, the medical data display screen 15 is output to the communication unit 33A by the screen output control unit 114 (step S120). As a result, the medical data display screen 15 is transmitted from the communication unit 33A to the client terminal 12. In the client terminal 12, the medical data display screen 15 shown in FIG. 9 is displayed on the display 34B.

As illustrated in FIG. 10, the doctor designates a desired item using the check box 80 of the medical data display screen 15, designates a desired period using the period designating bar 81, and clicks the calculation execution button 83. As a result, a display switching request including the designated data range, in which the item designated by using the check box 80 is a designated data item and the period designated by using the period designating bar 81 is a designated data period, is transmitted from the client terminal 12 to the medical assistance server 11.

The display 84 of recommended data items and the display 85 of a recommended data period are made on the medical data display screen 15 in FIG. 9 having a designated data range input function. The doctor designates a range while referring to the display 84 of recommended data items and the display 85 of a recommended data period. Therefore, since the doctor does not need to remember the recommended data ranges of all diagnostic assistance programs 101, it is possible to easily designate the same range as the recommended data range.

In addition, since the check box 80 for designating an item and the period designating bar 81 for designating a period are displayed as a designated data range input function on the medical data display screen 15 shown in FIG. 9, it is possible to check the display 84 of recommended data items and the display 85 of a recommended data period and the designation state of items and a period by the doctor while comparing them with each other. Therefore, since it is possible to reduce the burden of the doctor in the designation of a range, it is possible to improve work efficiency.

In the medical assistance server 11, the display switching request including the designated data range from the client terminal 12 is received by the communication unit 33A. The display switching request is output to the request receiving unit 110 from the communication unit 33A, and is received by the request receiving unit 110 (step S130). The designated data range of the display switching request is transmitted from the request receiving unit 110 to the medical data acquisition unit 111.

The medical data acquisition unit 111 extracts medical data corresponding to the designated data range of the display switching request from the medical data in the entire course of treatment for the patient, which is stored in the storage device 30A, and transmits the extracted medical data to the program control unit 112.

The program control unit 112 gives the medical data of the designated data range transmitted from the medical data acquisition unit 111, as input data, to the diagnostic assistance program 101 corresponding to the program ID transmitted from the request receiving unit 110, so that the calculation is performed (step S140). The diagnostic assistance information is output by executing the diagnostic assistance program 101 and performing calculation. The diagnostic assistance information is transmitted from the program control unit 112 to the screen generation unit 113.

In the screen generation unit 113, the medical data display screen 15 shown in FIG. 11 is generated based on the diagnostic assistance information. Then, the medical data display screen 15 is output to the communication unit 33A by the screen output control unit 114 (step S150). As a result, the medical data display screen 15 is transmitted from the communication unit 33A to the client terminal 12. In the client terminal 12, the medical data display screen 15 shown in FIG. 11 is displayed on the display 34B. The doctor performs diagnosis based on the diagnostic assistance information of the medical data display screen 15.

On the medical data display screen 15 shown in FIG. 11, the diagnostic assistance information, the display 84 of recommended data items and the display 85 of a recommended data period, and the designation state of designated data items and a designated data period using the check box 80 and the period designating bar 81 are displayed. Therefore, when performing diagnosis based on the diagnostic assistance information, the doctor can recognize whether or not the designated data range is different from the recommended data range.

In the medical data display screen 15, the examination image 24 and various kinds of data included in the electronic medical record 23 are collectively displayed as medical data within one screen. Therefore, it is possible to smoothly proceed with the diagnosis, compared with a case in which the electronic medical record 23 and the examination image 24 are viewed in separate display screens.

In addition, the medical data display screen 15 is a screen that is common to a plurality of diagnostic assistance programs 101 used in the medical assistance server 11. Therefore, usability is better than preparing a plurality of medical data display screens corresponding to the respective diagnostic assistance programs 101.

In the medical data display screen 15, medical data is displayed in the medical data display region 50 near the center of the screen, and diagnostic assistance information is displayed in the various information display region 54 located on the periphery of the screen. In the various information display region 54, a button prompting the confirmation of the diagnostic assistance information or a button for removing the display is not displayed. Therefore, the doctor can freely refer to the diagnostic assistance information without the stress of the button selection operation.

Figure 15:
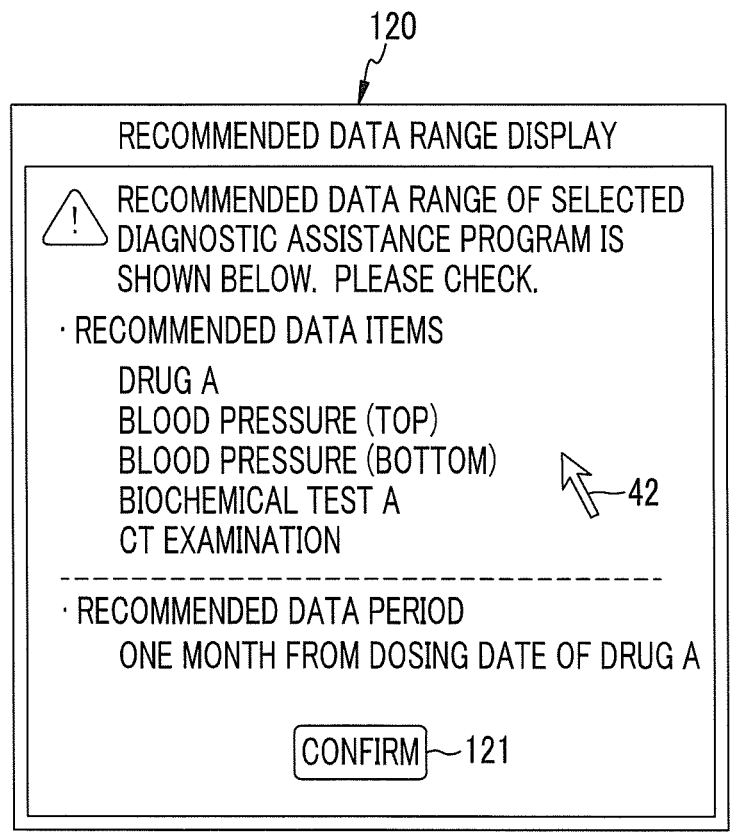
FIG. 15 is a diagram showing a recommended data range display screen on which only a recommended data range is displayed.

In the first embodiment described above, the medical data display screen also has a function of the recommended data range display screen. However, a recommended data range may be displayed on a separate screen. For example, the screen generation unit 113 may generate a recommended data range display screen 120 shown in FIG. 15 and transmit this to the client terminal 12 so as to pop up on the medical data display screen 15 shown in FIG. 9. A message prompting the confirmation of the recommended data range, specific content of the recommended data items and the recommended data period, and a confirm button 121 for, removing the display of the recommended data range display screen 120 are displayed on the recommended data range display screen 120. In FIG. 15, "drug A", "blood pressure (top), blood pressure (bottom)", "biochemical test A", and "CT examination" are displayed as the recommended data items, and "one month from the dosing date of drug A" is displayed as the recommended data period.

As means for notifying the doctor of the recommended data range, a sound of, for example, "read a message" may be output in addition to or instead of the displays 84 and 85 or the recommended data range display screen 120. In short, it is possible to use any kind of means as long as it is possible to notify the doctor of the recommended data range.

In the first embodiment described above, the recommended data range is defined as a range of input data for the diagnostic assistance program 101 to output the reliable diagnostic assistance information. However, the recommended data range is not limited to the range of input data for outputting the reliable diagnostic assistance information, and it is also possible to provide a margin to some extent. For example, the recommended data range may be configured to include an essential data range that is essential as a range to be used for input data and an allowable data range that is not essential as a range to be used for input data but is allowed.

Second Embodiment

When the recommended data range includes an essential data range and an allowable data range, if both the essential data range and the allowable data range are displayed as recommended data ranges without distinction when designating a range to be used for input data, the doctor recognizes both the essential data range and the allowable data range as essential data ranges. Therefore, in the present embodiment, the essential data range and the allowable data range are displayed so as to be distinguishable.

As shown in FIG. 16, in a recommended data range list 125 in the present embodiment, the recommended data items are divided into essential data items and allowable data items, and the recommended data period is divided into an essential data period and an allowable data period. The essential data range is formed by the essential data items and the essential data period, and the allowable data range is formed by the allowable data items and the allowable data period. In FIG. 16, for the "diagnostic assistance program (PR1)", "drug A", "blood pressure (top), blood pressure (bottom), pulse, body temperature", and "biochemical test A" are registered as essential data items, "drug B", "heart rate, and "biochemical test B, biochemical test C" are registered as allowable data items, "two weeks from the dosing date of drug A" is registered as an essential data period, and "three to four weeks from the dosing date of drug A" is registered as an allowable data period.

Figure 17:
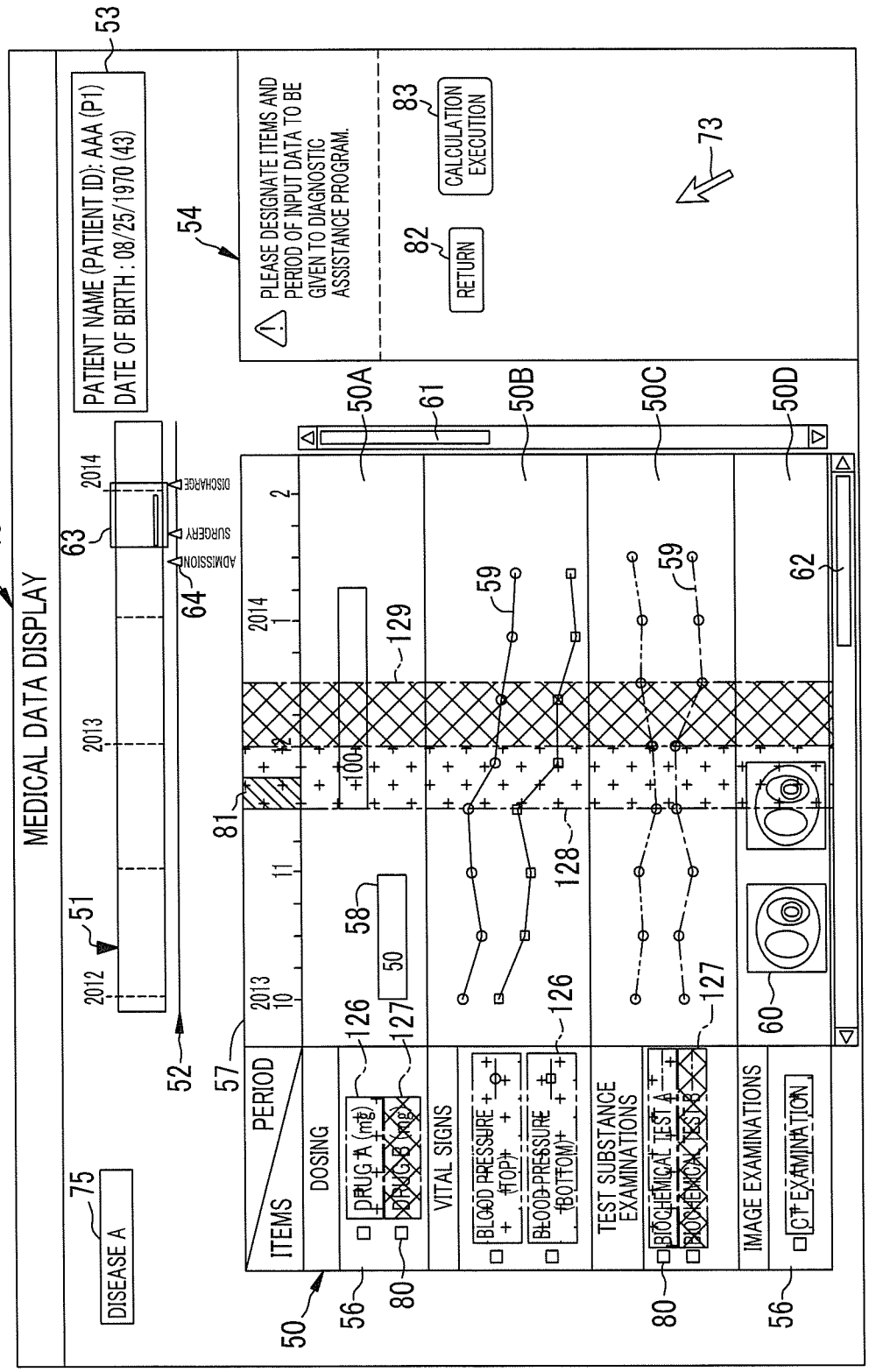
FIG. 17 is a diagram showing a medical data display screen on which an essential data range and an allowable data range are displayed so as to be distinguishable.

In this case, the screen generation unit 113 generates the medical data display screen 15 shown in FIG. 17 instead of the medical data display screen 15 shown in FIG. 9. The medical data display screen 15 is basically the same display content as the medical data display screen 15 shown in FIG. 9, but is different from the medical data display screen 15 shown in FIG. 9 in that the essential data range and the allowable data range are displayed so as to be distinguishable. Specifically, similar to the recommended data item of the medical data display screen 15 shown in FIG. 9, each essential data item is highlighted with a different color (for example, pink fluorescent color when the color of the background is gray) from the background of the item display column 56, as surrounded by the one-dot chain line given with reference numeral 126 and shown by cross hatching. On the other hand, each allowable data item is highlighted with a different color (for example, orange fluorescent color when the color of the background is gray) from the essential data item, as surrounded by the one-dot chain line given with reference numeral 127 and shown by lattice hatching. In addition, similar to the recommended data period of the medical data display screen 15 shown in FIG. 9, the essential data period is highlighted with a different color (for example, pink fluorescent color when the color of the background is gray) from the background, as surrounded by the one-dot chain line given with reference numeral 128 and shown by cross hatching. On the other hand, the allowable data period is highlighted with a different color (for example, orange fluorescent color when the color of the background is gray) from the essential data period, as surrounded by the one-dot chain line given with reference numeral 129 and shown by lattice hatching.

In FIG. 17, "drug A", "blood pressure (top), blood pressure (bottom)", "biochemical test A", and "CT examination" are displayed as the essential data items, and "two weeks from the dosing date of drug A" is displayed as the essential data period. In addition, "drug B" and "biochemical test B" are displayed as the allowable data items, and "three to four weeks from the dosing date of drug A" is displayed as the allowable data period.

Thus, since the essential data range and the allowable data range are displayed so as to be distinguishable, the doctor can see that it is sufficient to designate at least the essential data range. Accordingly, there is no confusion in the designation of a range.

As illustrated in FIG. 10, recommended data items and the designated data items designated by the check box 80 and a recommended data period and the designated data period designated by the period designating bar 81 may be different. Since the content of diagnostic assistance information may change depending on the range to be used for input data, the doctor may want to designate a different range from the recommended data range as a range to be used for input data. In order to meet such circumstances, it may be allowed that there is a difference between the designated data range and the recommended data range.

Figure 18:
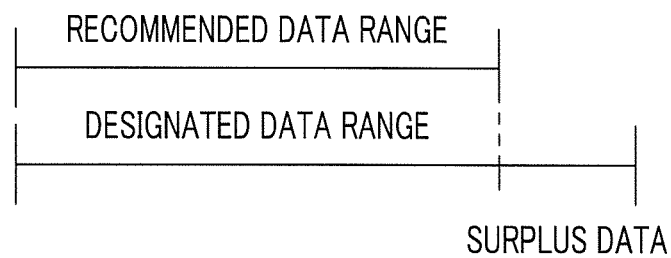
FIG. 18 is an explanatory view showing a case in which there is surplus data which is medical data outside the recommended data range and inside the designated data range.
Figure 19:
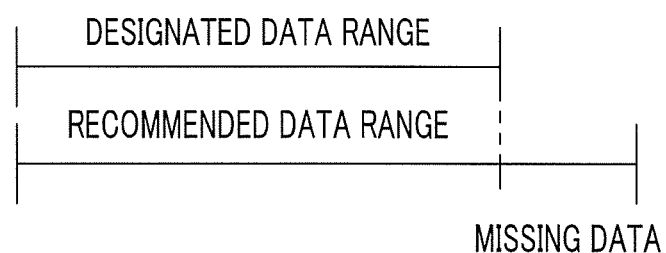
FIG. 19 is an explanatory view showing a case in which there is missing data which is medical data outside the designated data range and inside the recommended data range.

There are two cases in which there is a difference between the designated data range and the recommended data range. That is, these are a case in which there is surplus data, which is medical data outside the recommended data range and inside the designated data range as shown in FIG. 18 in a simplified manner and a case in which there is missing data which is medical data outside the designated data range and inside the recommended data range as shown in FIG. 19 in a simplified manner.

When there is surplus data, the program control unit 112 executes the diagnostic assistance program 101 using only the medical data of the recommended data range as input data without using the surplus data as input data, for example. When there is missing data, the program control unit 112 executes the diagnostic assistance program 101 using only the medical data of the designated data range as input data, for example.

In this case, in the diagnostic assistance information when there is surplus data, some of the items or a part of the period designated by the doctor is not used as input data. The diagnostic assistance information when there is missing data is output in a state in which data is deficient compared with the recommended data range. That is, even though there is input data that should be included in the calculation, diagnostic assistance information may be output by force. Therefore, it is hard to say that the diagnostic assistance information in these cases is reliable. However, since the doctor designates a different range from the recommended data range after recognizing these points, there is no possibility that the doctor will perform diagnosis by mistakenly believing that the item or the period designated by the doctor himself or herself is used for the output of diagnostic assistance information or that the doctor will perform diagnosis by mistakenly believing that diagnostic assistance information is reliable.

Third Embodiment

However, when there is missing data, if the diagnostic assistance program 101 is executed using only the medical data of the designated data range, significantly unreliable diagnostic assistance information may be output. In this case, since it is not possible to use the diagnostic assistance information for diagnosis, it is meaningless to execute the diagnostic assistance program 101. Therefore, in the present embodiment, even if there is missing data, diagnostic assistance information that is reliable to some extent is output to the diagnostic assistance program 101 by supplementing the missing data with appropriate supplementary data.

Figure 20:
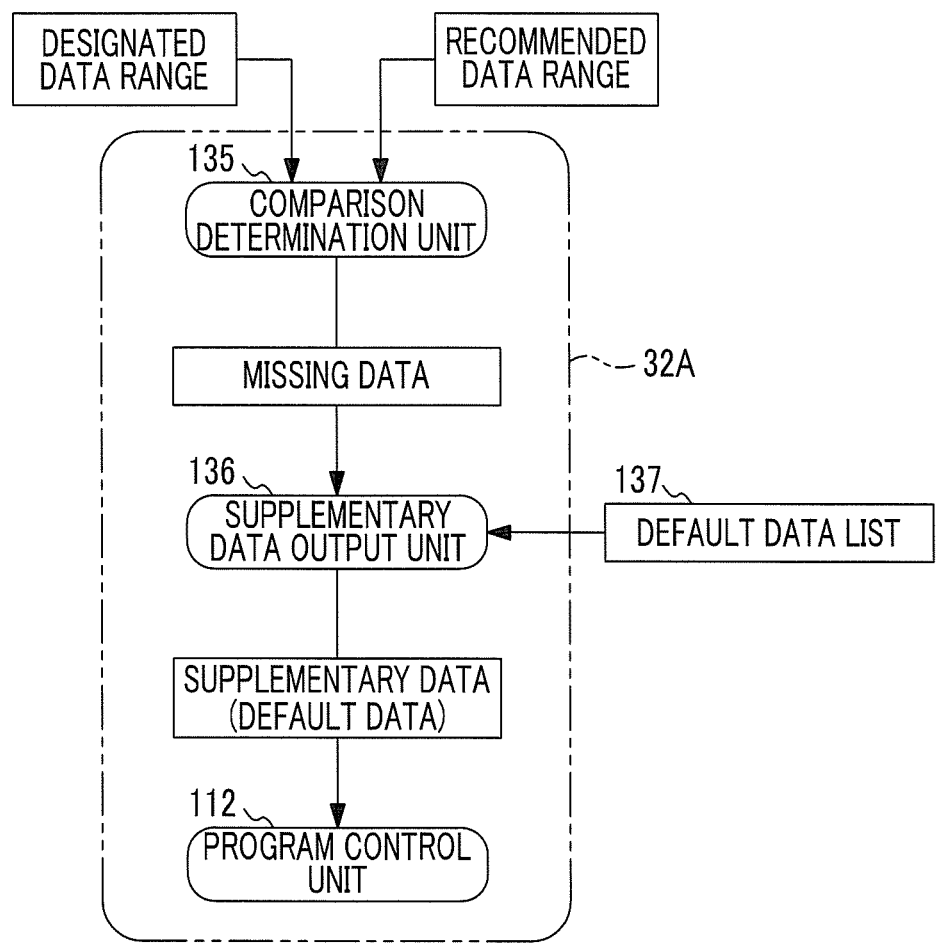
FIG. 20 is a block diagram showing a CPU of a medical assistance server including a supplementary data output unit in a third embodiment.

In FIG. 20, the CPU 32A of the medical assistance server of the present embodiment includes a comparison determination unit 135 and a supplementary data output unit 136 in addition to the functional units (not shown except for the medical data acquisition unit 111 and the program control unit 112) of the first embodiment described above. The comparison determination unit 135 receives the designated data range from the request receiving unit 110 and the recommended data range from the recommended data range output unit 115, and compares these ranges with each other. The comparison determination unit 135 determines whether or not there is a difference between the designated data range and the recommended data range. When there is a difference between the designated data range and the recommended data range, the comparison determination unit 135 picks up the missing data, which is medical data missing in the designated data range, from the medical data designated in the recommended data range. The comparison determination unit 135 outputs the information of the picked missing data to the supplementary data output unit 136.

The supplementary data output unit 136 outputs default data of a default data list 137 to the program control unit 112 as supplementary data to supplement the missing data from the comparison determination unit 135. The program control unit 112 executes the diagnostic assistance program 101 by using data, which is obtained by adding the supplementary data to the medical data of the designated data range, as input data.

The default data list 137 is stored in the storage device 30A in advance. As shown in FIG. 21, default data for each item of the medical data is registered in the default data list 137. The default data is data that can be applied in common to a plurality of patients. For example, items of dosing are a standard dose and a standard dosing period that are set for each drug, items of vital signs are average blood pressure, normal temperature, or average pulse of an adult, and items of test substance examinations are average examination values. The supplementary data output unit 136 reads default data, which matches the items of missing data, from the default data list 137, and outputs the read default data as supplementary data.

Figure 22:
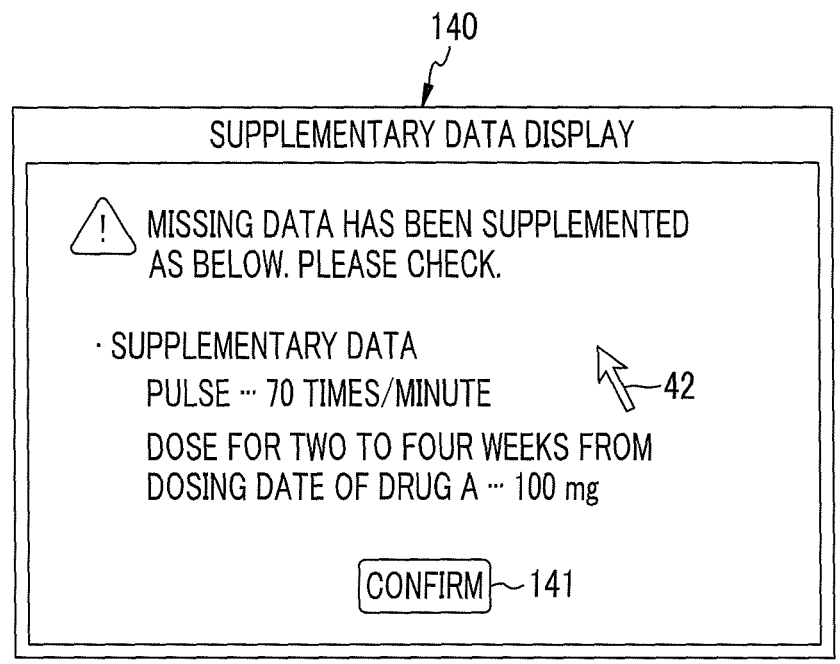
FIG. 22 is a diagram showing a supplementary data display screen.

In this case, the screen generation unit 113 generates a supplementary data display screen 140 shown in FIG. 22. In FIG. 22, a message showing that there is missing data and that this has been supplemented with supplementary data is displayed on the supplementary data display screen 140. In addition, the specific content of the supplementary data is displayed on the supplementary data display screen 140. The supplementary data display screen 140 pops up on the medical data display screen 15 shown in FIG. 11. In FIG. 22, "70 times/minute" is illustrated as supplementary data of "pulse", and "100 mg" is illustrated as supplementary data of "dose of two to four weeks from the dosing date and time of drug A". In addition, a confirm button 141 is a button for removing the display of the supplementary data display screen 140.

According to the medical assistance system of the present embodiment, since the missing data is supplemented with supplementary data if there is the missing data, diagnostic assistance information that is reliable to some extent can be output to the diagnostic assistance program 101. Therefore, it is possible to reduce a possibility of the execution of the diagnostic assistance program 101 becoming useless due to the output of the significantly unreliable diagnostic assistance information. In addition, since the supplementary data display screen 140 is displayed, it is possible to notify the doctor that the diagnostic assistance information is not reliable, and it is possible to notify the doctor of which kind of data has been used as supplementary data. If the doctor determines that the value of the displayed supplementary data is not so different from the value of the patient who is currently examined, it is possible to determine that there is no influence on the reliability of the diagnostic assistance information and make a diagnosis based on the diagnostic assistance information. If the doctor determines that the value of the supplementary data is greatly different from the value of the patient, it is possible to designate a range again and to make the diagnostic assistance program 101 output the diagnostic assistance information again.

In recent years, the selection of drugs for each patient according to the genetic test information of each patient has been considered. However, all patients do not necessarily undergo genetic testing. Therefore, when the diagnostic assistance program 101 has been developed according to the algorithm using genetic test information and the genetic test information has been registered as the recommended data item, a case occurs in which there is no genetic test information depending on a patient and this becomes missing data. When presenting the recommended drugs based on genetic test information as diagnostic assistance information, if it is specified that the genetic test information is missing data and that this has been supplemented with supplementary data, it is possible to notify the doctor of whether or not the recommended drugs are based on the genetic test information of the patient. In this case, it is possible to take measures, such as starting the diagnostic assistance program 101 again after performing genetic testing additionally and then selecting drugs corresponding to the genetic test information. Accordingly, this is user-friendly for the doctor.

In addition, default data may be registered for each of small classifications, such as patient attributes including the sex, age, body type, residential area, and nationality of the patient and diseases which the patient suffers from. For example, "36.5° C." is registered as the default data of body temperature of an adult, and "37.0° C." that is slightly higher than "36.5° C." is registered as the default data of body temperature of an infant. In this manner, it is possible to further improve the reliability of the diagnostic assistance information when there is missing data.

Fourth Embodiment

Instead of the default data, estimated data that is estimated for each patient based on the medical data may be used as supplementary data.

Figure 23:
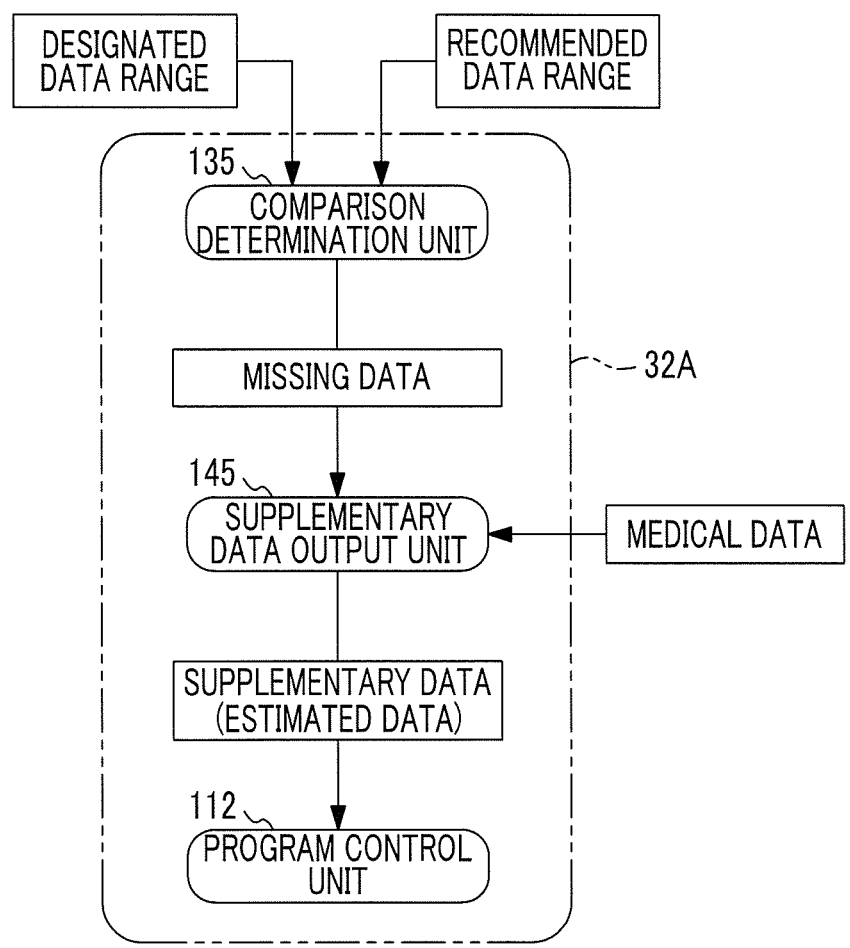
FIG. 23 is a block diagram showing a CPU of a medical assistance server including a supplementary data output unit in a fourth embodiment.

In FIG. 23, a supplementary data output unit 145 of the CPU 32A of the medical assistance server of the present embodiment receives information regarding the missing data from the comparison determination unit 135, and receives the medical data in the entire course of treatment for the patient from the medical data acquisition unit 111. The supplementary data output unit 145 estimates the missing data from the medical data, and outputs the estimated data to the program control unit 112 as supplementary data. As in the third embodiment described above, the program control unit 112 executes the diagnostic assistance program 101 by using the medical data of the designated data range and the supplementary data as input data.

If the missing data is, for example, measured values of vital signs or examination values of test substance examinations, the supplementary data output unit 145 extracts measured values of vital signs or examination values of test substance examinations in a certain period from the medical data, calculates the average value, and sets the average value as estimated data. Also by using the estimated data as supplementary data, the same effect as in the third embodiment described above is obtained. In addition, since the estimated data is estimated from the medical data of a target patient unlike default data, it is possible to further improve the reliability of the diagnostic assistance information when there is missing data. In addition, since it is not necessary to store the default data, it is possible to reduce the capacity load of the storage device 30A.

The present embodiment and the third embodiment may be combined. In this case, estimated data may be used as missing data that can be estimated from other medical data, and default data may be used as missing data that cannot be estimated.

When there is data corresponding to data that is required for the execution of a diagnostic assistance program but is missing (missing data) in the medical data in the entire course of treatment for the patient, which is acquired in response to the acquisition request and is stored in the storage device 30A, it is preferable to extract medical data corresponding to the missing data and set the medical data as supplementary data. In addition, only when there is no data corresponding to the missing data in the entire course of treatment for the patient, default data or estimated data may be set as supplementary data.

Instead of the pop-up display of the supplementary data display screen 140 on the medical data display screen 15 in FIG. 11, the supplementary data display screen 140 may be displayed before executing the diagnostic assistance program 101 so that the doctor selects whether to continue the calculation.

Although one computer that forms the medical assistance server 11 is made to operate as a medical assistance device in each of the embodiments described above, a plurality of computers may have the respective functions of the medical assistance device in a distributed manner. For example, in order to improve the processing capacity or reliability, the medical assistance server 11 may be formed by a plurality of server computers that are separated from each other as hardware. Specifically, the medical assistance server 11 is formed by two server computers, that is, a server computer including the request receiving unit 110, the medical data acquisition unit 111, and the program control unit 112 and a server computer including the screen generation unit 113, the screen output control unit 114, and the recommended data range output unit 115. Alternatively, the client terminal 12 may be made to have some or all of the functions of the request receiving unit 110 and the like. Thus, the hardware configuration of a computer can be appropriately changed according to the required performance, such as processing capacity, safety, or reliability.

Needless to say, in order to ensure the safety or reliability, an application program, such as the operation program 100, may be duplicated or may be stored in a plurality of storage devices in a distributed manner, without being limited to hardware.

Fifth Embodiment

Figure 24:
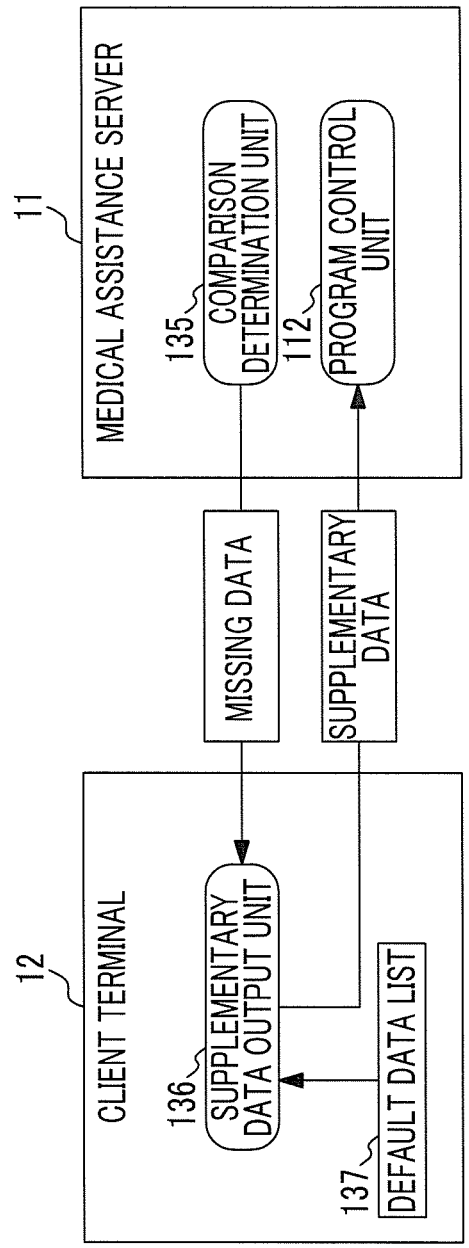
FIG. 24 is a block diagram showing the configuration in which a supplementary data output unit is provided in a client terminal in a fifth embodiment.

FIG. 24 shows an example in which the supplementary data output unit 136 of the third embodiment is provided in the client terminal 12. The default data list 137 is stored in the storage device 30B (not shown) of the client terminal 12.

The comparison determination unit 135 outputs information regarding missing data to the communication unit 33A of the medical assistance server 11. As a result, the missing data is transmitted from the communication unit 33A to the client terminal 12. The supplementary data output unit 136 outputs supplementary data to the communication unit 33B of the client terminal 12. As a result, the supplementary data is transmitted to the medical assistance server 11. The supplementary data is transmitted to the program control unit 112 in the medical assistance server 11. Subsequent processing is the same as in the third embodiment described above. In addition, the supplementary data output unit 145 of the fourth embodiment may be provided in the client terminal 12.

Sixth Embodiment

Figure 25:
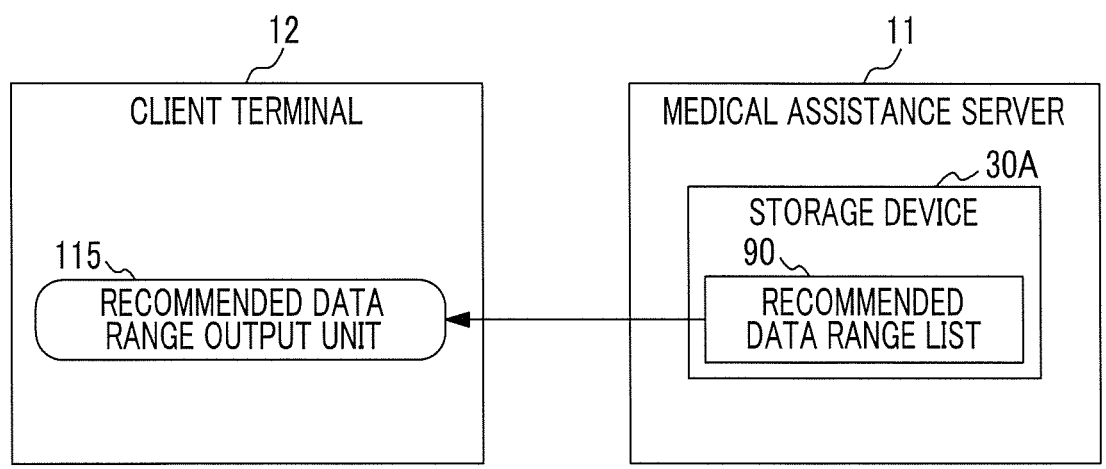
FIG. 25 is a block diagram showing the configuration in which a recommended data range output unit is provided in a client terminal in a sixth embodiment.

FIG. 25 shows an example in which the recommended data range output unit 115 is provided in the client terminal 12. Although not shown, the screen generation unit 113 and the screen output control unit 114 are also provided in the client terminal 12. In this case, the client terminal 12 asks the medical assistance server 11 about the recommended data range corresponding to the diagnostic assistance program 101 that the doctor has selected as a program to be used. The medical assistance server 11 transmits the recommended data range from the recommended data range list 90 stored in the storage device 30A to the client terminal 12 through the communication unit 33A. The recommended data range output unit 115 acquires the recommended data range received by the communication unit 33B of the client terminal 12. Thus, the recommended data range output unit 115 may read the recommended data range from the recommended data range list 90 in the built-in storage device 30 as in the first embodiment described above, or may receive the recommended data range from the external storage device 30 as in the present embodiment.

When the client terminal 12 has a function of a medical assistance device, the request receiving unit 110 receives the same request as the distribution request or the display switching request in the first embodiment described above by the operation instruction from the input device 35B through the operation screen displayed on the display 34B of the client terminal 12. The screen output control unit 114 outputs various operation screens including the medical data display screen 15 to the display 34B of the client terminal 12.

Although the medical assistance system 10 constructed in the medical facility is illustrated and the medical assistance server 11 is used in one medical facility in each of the embodiments described above, the medical assistance server 11 may be used in a plurality of medical facilities.

In each of the embodiments described above, the medical assistance server 11 is communicably connected to the client terminal 12 installed in one medical facility through the network 14, such as a LAN, and provides application services called medical assistance in response to the request from the client terminal 12. In order to make the medical assistance server 11 available in a plurality of medical facilities, the medical assistance server 11 is communicably connected to each client terminal 12 installed in the plurality of medical facilities, for example, through a wide area network (WAN), such as the Internet or a public communication network. Then, the medical assistance server 11 receives requests from the client terminals 12 in the plurality of medical facilities through the WAN, and provides application services for medical assistance to the client terminals 12. When using a WAN it is preferable to build a virtual private network (VPN) or to use a communication protocol with a high security level, such as hypertext transfer protocol secure (HTTPS), in consideration of information security. In this case, the installation location and management entity of the medical assistance server 11 may be a data center managed by a company that is different from the medical facilities, or may be one of the plurality of medical facilities, for example.

In each of the embodiments described above, both the range of each item determined by item designation, such as the designated data item and the recommended data item, and a period determined by the designation of a temporal range, such as the designated data period and the recommended data period, are illustrated as a range to be used for the input data that is input to the diagnostic assistance program 101. However, at least one of the range of the item and the period may be used.

In the first embodiment described above, the medical data display screen 15 also serves as a screen for designating the designated data range. However, it is also possible to generate the screen for designating the designated data range separately from the medical data display screen 15. In the first embodiment described above, a patient ID is input on the startup screen, and a disease is selected on the medical data display screen 15 shown in FIG. 6. However, the input of a patient ID and the selection of a disease may be performed on one screen.

In addition, medical data in the entire course of treatment for the patient is displayed on the medical data display screen 15 shown in FIG. 6, diagnostic assistance program 101 and medical data corresponding to the display items set in the disease-specific list 80 are displayed on the medical data display screen 15 shown in FIG. 7, and display items and the diagnostic assistance program 101 are narrowed down by the selection of the disease. However, such narrowing down may not be performed. In the various information display region 54 of the medical data display screen 15 shown in FIG. 6, the names of all diagnostic assistance programs 101 that can be used in the medical assistance server 11 are listed. However, considering that the number of diagnostic assistance programs 101 will increase in the future, narrowing down the display items or the available diagnostic assistance programs 101 for each disease as in the first embodiment is preferable because it becomes easy to designate an item or to select the diagnostic assistance program 101.

Without being limited to the disease, when the medical assistance server 11 for each patient or each medical department, such as surgery, internal medicine, pediatrics, and ophthalmology, is used in a plurality of medical facilities, display items and the diagnostic assistance program 101 may be set according to the medical unit, such as a medical facility, an event (for example, admission and discharge dates or surgery date), a medical phase that is a progressive stage (for example, examination stages such as a first visit, an image examination, and a test substance examination, or progression of cancer or diabetes) of treatment or disease, or a medical purpose such as the malignancy determination of a tumor, reduction effect determination, side effects determination of drugs, and size measurement of a lesion. If the display items and the diagnostic assistance program 101 are set in a multiple manner for each disease and each medical department, it is possible to further narrow down the display items and the diagnostic assistance program 101. Therefore, it becomes easier to designate an item and to select the diagnostic assistance program 101.

In the first embodiment described above, candidates for the diagnostic assistance program 101 to be used are displayed on the medical data display screen 15 shown in FIG. 7 after the selection of a disease, and the selection of the diagnostic assistance program 101 to be used is received. However, the invention is not limited thereto. For example, the medical data display screen 15 shown in FIG. 11 may be displayed by executing one typical diagnostic assistance program 101 automatically with the medical data of the recommended data range as input data after the selection of a disease, and then the designation of a range may be received. In the medical data display screen 15 shown in FIG. 11, the check box 80 and the period designating bar 81 are provided, and the display 84 of the recommended data item and the display 85 of the recommended data period are further performed. The typical diagnostic assistance program 101 is registered in advance in the disease-specific list 80. In this case, if the doctor is satisfied with diagnostic assistance information according to the typical diagnostic assistance program 101, an unnecessary operation, such as the designation of a range or the selection of the diagnostic assistance program 101, is not required. If the doctor is not satisfied with diagnostic assistance information according to the typical diagnostic assistance program 101, it is possible to receive the designation of a range.

In addition, the diagnostic assistance program 101 is not always used but is used in a limited case, such as when a doctor performs difficult determination. Therefore, it is not user-friendly to make a doctor select the diagnostic assistance program 101 each time. For this reason, first, the typical diagnostic assistance program 101 is automatically executed to display the diagnostic assistance information, so that the doctor designates a range by selecting the diagnostic assistance program 101 only when the diagnostic assistance information is required and the doctor continues treatment by neglecting the diagnostic assistance information when the diagnostic assistance information is not required. In this manner, the screen operation becomes simple, and is not cumbersome.

Thus, cases of the selection of the diagnostic assistance program 101 to be used include a case in which the candidate for the diagnostic assistance program 101 is directly selected as in the first embodiment described above and a case in which the diagnostic assistance program 101 to be used is indirectly selected by selecting a different option (for example, a disease) from the diagnostic assistance program 101. In addition, options different from the diagnostic assistance program 101 may be other medical units, such as a patient, medical department, medical facility, event, medical phase, and medical purpose, without being limited to the disease.

As the diagnostic assistance program 101 to be used, only one diagnostic assistance program 101 may be selectable as in the first embodiment described above, or a plurality of diagnostic assistance programs 101 may be selectable. When a plurality of diagnostic assistance programs 101 are selectable, a recommended data range is displayed and a range is designated for each of the selected diagnostic assistance program 101.

As an examination image to be distributed as medical data from the image server 22 to the medical assistance server 11, the entire examination image may be selected, or a partial region of the examination image, for example, a region of interest surrounding the lesion reflected in the examination image, may be selected.

Not only the diagnostic assistance information of the target patient whose patient ID has been input on the startup screen but also the diagnostic assistance information of other patients who have the same disease and have similar symptoms may be output. In this case, in addition to the request for acquisition of medical data of the target patient, the medical data acquisition unit 111 outputs a request for acquisition of medical data of a patient having measurement values of vital signs or examination values of test substance examinations similar to those of the target patient or a patient having a lesion size and a lesion type similar to that of the target patient, for example. The program control unit 112 outputs diagnostic assistance information based on not only the medical data of the target patient but also the medical data of other patients. Thus, by outputting not only the diagnostic assistance information of the target patient but also the diagnostic assistance information of other patients who have the same disease and have similar symptoms, it is possible to perform diagnosis in a shorter time.

When medical units including a disease or a medical purpose are selected as in the pull-down menu 55 for selecting the disease in the first embodiment and the display is switched on the medical data display screen having the check box 80, such as the medical data display screen 15 shown in FIG. 9, a check mark may be put in advance in the check boxes 80 of items that are common in the medical unit. The items that are common in the medical unit are items common to the recommended data items of a plurality of diagnostic assistance programs 101 when there is a plurality of diagnostic assistance programs 101 corresponding to a certain disease, for example. Such common items are registered in advance for each medical unit, and a check mark is put in the check boxes 80 of the common items when the screen generation unit 113 generates the medical data display screen 15 and then the medical data display screen 15 is transmitted to the screen output control unit 114. In this manner, since some items are already selected from the beginning, it is possible to improve work efficiency when a doctor edits items to be designated by adding or removing an item as necessary. When there is only one diagnostic assistance program 101 corresponding to the medical unit, a check mark is put in the check box 80 of the item used in the one diagnostic assistance program 101 in advance. Therefore, since a doctor does not have to do editing, work efficiency is good.

The recommended data range setting information is not limited to the list form in which the recommended data ranges of the respective diagnostic assistance programs 101 are collected, such as the recommended data range list 90 shown in the first embodiment, and each diagnostic assistance program 101 may hold the recommended data range.

It is needless to say that the invention is not limited to the above embodiments and various configurations can be adopted without departing from the scope of the invention. In addition, it is also possible to appropriately combine the above-described various embodiments or various modifications. In addition to the program, the invention also extends to a storage medium for storing the program.

What is claimed is:

1. A medical assistance device, comprising:
   a storage device, storing medical data of a patient, a plurality of diagnostic assistance programs, and a recommended set of data list recording recommended data items and recommended data periods that are corresponding to the plurality of diagnostic assistance programs, wherein the medical data is acquired from an external server group in response to a distribution request; and
   a processor, configured to function as
   a screen generation unit, a program selection receiving unit and a recommended set of data output unit,
   wherein the screen generation unit generates a medical data display screen to display the medical data of the patient, wherein the medical data display screen comprising
      an item display column;
      a period display column; and
      a various information display region;
   wherein the program selection receiving unit receives a selection of a diagnostic assistance program among the plurality of diagnostic assistance programs made by a user,
   wherein the recommended set of data output unit outputs a recommended set of data to the medical data display screen, the recommended set of data comprising the recommended data item and the recommended data period recorded in the recommended set of data list, wherein the recommended set of data corresponding to the selected diagnostic assistance program received by the program selection receiving unit,
   wherein the recommended set of data output unit outputs the recommended data item to the item display column of the medical data display screen, the recommended set of data output unit outputs the recommended data period to the period display column of the medical data display screen, wherein the recommended data item in the item display column to be used for items of the medical data, and the recommended data period in the period display column is a period to be used for a plurality of pieces of the medical data on their collection time for an entire course of treatment for the patient,
   wherein the processor, in response to receiving a designated set of data obtained through an interaction on the medical data display screen, is configured to execute the selected diagnostic assistance program by using the designated set of data in the medical data as the input data to generate diagnostic assistance information after the recommended set of data is output from the recommended set of data output unit, wherein the diagnostic assistance information is used for assisting diagnosis of the patient,
   wherein the designated set of data comprises a designated data item and a designated data period selected by the user, wherein the designated data item is selected from the recommended data items in the item display column, and the designated data period is selected from the recommended data period in the period display column,
   wherein the processor outputs the diagnostic assistance information to the various information display region of the medical data display screen.

2. The medical assistance device according to claim 1, wherein the recommended set of data includes an essential set of data, which is essential data to be used as the input data, and an allowable set of data, which is not essential data to be used as the input data but is allowed, and
   the essential set of data and the allowable set of data are displayed in different forms on the medical data display screen.

3. The medical assistance device according to claim 1, wherein the medical data display screen is common to the plurality of diagnostic assistance programs.

4. The medical assistance device according to claim 1, the processor further configured to function as a supplementary data output unit that, in a case where missing data that is data outside the designated set of data and inside the recommended set of data is present, outputs supplementary data to supplement the missing data,
   wherein the processor is configured to execute the selected diagnostic assistance program using data, which is obtained by adding the supplementary data to the designated set of data, as the input data.

5. The medical assistance device according to claim 4, wherein the supplementary data is default data that is set in advance and is applicable in common to a plurality of the patients.

6. The medical assistance device according to claim 4, wherein the supplementary data is estimated for each patient of a plurality of patients based on the medical data of each patient.

7. The medical assistance device according to claim 1,
wherein the diagnostic assistance programs are registered in advance for each of at least one of the patient, a disease which the patient suffers from, a department, a medical facility, an event that occurs in a course of treatment for the patient, a medical phase that is a progressive stage of treatment or disease, and a medical purpose,
wherein the program selection receiving unit receives a selection of the at least one of the patient, the disease which the patient suffers from, the department, the medical facility, the event that occurs in the course of the treatment for the patient, the medical phase that is a progressive stage of treatment or disease, and the medical purpose, and
the processor is further configured to execute the diagnostic assistance program corresponding to the selection of the at least one of the patient, the disease which the patient suffers from, the department, the medical facility, the event that occurs in the course of the treatment for the patient, the medical phase that is a progressive stage of treatment or disease, and the medical purpose.

8. An operation method of a medical assistance device, comprising:
obtaining medical data of a patient from an external server group in response to a distribution request;
displaying a medical data display screen, wherein the medical data display screen comprising:
an item display column;
a period display column; and
a various information display region;
receiving a selection of a diagnostic assistance program among a plurality of diagnostic assistance programs made by a user;
outputting a recommended set of data to the medical data display screen, the recommended set of data comprising a recommended data item and a recommended data period recorded in a recommended set of data list, wherein the recommended set of data corresponding to the selected diagnostic assistance program,
wherein the recommended data item is output to the item display column of the medical data display screen, and the recommended data period is output to the period display column of the medical data display screen, wherein the recommended data item in the item display column to be used for items of the medical data, and the recommended data period in the period display column is a period to be used for a plurality of pieces of the medical data on their collection time for an entire course of treatment for the patient; and
in response to receiving a designated set of data obtained through an interaction on the medical data display screen, executing the selected diagnostic assistance program by using the designated set of data in the medical data as the input data to generate diagnostic assistance information after the output of the recommended set of data, wherein the designated set of data comprises a designated data item and a designated data period, wherein the diagnostic assistance information is used for assisting diagnosis of the patient,
wherein the diagnostic assistance information is output to the various information display region of the medical data display screen,
wherein the designated set of data comprises a designated data item and a designated data period selected by the user, wherein the designated data item is selected from the recommended data items in the item display column, and the designated data period is selected from the recommended data period in the period display column.

9. A non-transitory computer-readable recording medium on which an operation program for a medical assistance device is recorded,
wherein the program causes a computer to execute:
a display function of displaying a medical data display screen, wherein the medical data display screen comprising:
an item display column;
a period display column; and
a various information display region;
a program selection reception function of receiving a selection of a diagnostic assistance program among a plurality of diagnostic assistance programs made by a user;
a recommended set of data output function of outputting a recommended set of data to the medical data display screen, the recommended set of data comprising a recommended data item and a recommended data period recorded in a recommended set of data list, the recommended set of data corresponding to the selected diagnostic assistance program received through the program selection reception function, wherein the recommended data item is output to the item display column, and the recommended data period is output to the period display column; and
a selected diagnostic assistance program execution function of, in response to receiving a designated set of data obtained through an interaction on the medical data display screen, executing the selected diagnostic assistance program by using the designated set of data in the medical data as the input data to generate diagnostic assistance information after the output of the recommended set of data through the recommended set of data output function, wherein the designated set of data comprises a designated data item and a designated data period, wherein the diagnostic assistance information is used for assisting diagnosis of the patient,
wherein the diagnostic assistance information is output to the various information display region,
wherein the designated set of data comprises a designated data item and a designated data period selected by the user, wherein the designated data item is selected from the recommended data items in the item display column, and the designated data period is selected from the recommended data period in the period display column.

10. A medical assistance system, comprising:
a medical assistance server;
a client terminal;
a network that communicably connects the medical assistance server and the client terminal to each other; and
a medical assistance device, comprising:
a storage device, storing medical data of a patient, a plurality of diagnostic assistance programs, and a recommended set of data list recording recommended data items and recommended data periods that are corresponding to the plurality of diagnostic assistance programs, wherein the medical data is acquired from the medical assistance server in response to a distribution request from the client terminal; and
a processor, configured to function as a screen generation unit, a program selection receiving unit and a recommended set of data output unit;

wherein the screen generation unit generates a medical data display screen to display the medical data of the patient, wherein the medical data display screen a comprising:
an item display column;
a period display column; and
a various information display region,
wherein the program selection receiving unit receives a selection of a diagnostic assistance program among the plurality of diagnostic assistance programs made by a user,
wherein the recommended set of data output unit outputs a recommended set of data to the medical data display screen, wherein the recommended set of data comprising a recommended data item and a recommended data period recorded in the recommended set of data list, the recommended set of data corresponding to the selected diagnostic assistance program received by the program selection receiving unit, wherein the recommended set of data output unit outputs the recommended data item to the item display column of the medical data display screen, the recommended set of data output unit outputs the recommended data period to the period display column of the medical data display screen, wherein the recommended data item in the item display column to be used for items of the medical data, and the recommended data period in the period display column is a period to be used for a plurality of pieces of the medical data on their collection time for an entire course of treatment for the patient,
wherein the processor, in response to receiving a designated set of data obtained through an interaction on the medical data display screen, is further configured to execute the selected diagnostic assistance program by using the designated set of data in the medical data as the input data to generate the diagnostic assistance information after the recommended set of data is output from the recommended set of data output unit, wherein the diagnostic assistance information is used for assisting diagnosis of the patient,
wherein the designated set of data comprises a designated data item and a designated data period selected by the user, wherein the designated data item is selected from the recommended data items in the item display column, and the designated data period is selected from the recommended data period in the period display column,
wherein the processor outputs the diagnostic assistance information to the various information display region.

11. The medical assistance system according to claim 10, the processor of the medical assistance device is further configured to execute a supplementary data output unit,
wherein the supplementary data output unit, in a case where missing data that is data outside the designated set of data and inside the recommended set of data is present, outputs supplementary data to supplement the missing data, and
wherein the processor is further configured to execute the selected diagnostic assistance program using data, which is obtained by adding the supplementary data to the designated set of data, as the input data.

12. The medical assistance system according to claim 10, the client terminal further comprising a processor,
wherein the processor of the client terminal is configured to execute a supplementary data output unit,
wherein the supplementary data output unit, in a case where missing data that is data outside the designated set of data and inside the recommended set of data is present, outputs supplementary data to supplement the missing data,
wherein the medical assistance server transmits the missing data to the client terminal, and the client terminal transmits the supplementary data to the medical assistance server, and
wherein the processor of the medical assistance device is further configured to execute the selected diagnostic assistance program using data, which is obtained by adding the supplementary data to the designated set of data, as the input data.

13. The medical assistance device according to claim 1,
wherein the processor is further configured to display a screen of selecting the diagnostic assistance program that is executed to output the diagnostic assistance information, among the plurality of diagnostic assistance programs.

* * * * *